(12) United States Patent
Wainwright et al.

(10) Patent No.: US 10,465,228 B2
(45) Date of Patent: **\*Nov. 5, 2019**

(54) FILTRATION SYSTEM AND USE THEREOF

(71) Applicant: Charles River Laboratories, Inc., Wilmington, MA (US)

(72) Inventors: Norman R. Wainwright, Johns Island, SC (US); Dana M. Nutter, Charleston, SC (US); Eric Stimpson, Charleston, SC (US); Al Fuchs, Charleston, SC (US); Thomas Preidel, Uslar (DE)

(73) Assignee: Charles River Laboratories, Inc., Wilmington, MA (US)

( * ) Notice: Subject to any disclaimer, the term of this patent is extended or adjusted under 35 U.S.C. 154(b) by 274 days.

This patent is subject to a terminal disclaimer.

(21) Appl. No.: 15/457,294

(22) Filed: Mar. 13, 2017

(65) Prior Publication Data
US 2017/0183707 A1    Jun. 29, 2017

Related U.S. Application Data

(63) Continuation of application No. 14/858,495, filed on Sep. 18, 2015, now Pat. No. 9,624,463, which is a
(Continued)

(51) Int. Cl.
*B01D 29/085* (2006.01)
*C12Q 1/24* (2006.01)
(Continued)

(52) U.S. Cl.
CPC ............. *C12Q 1/24* (2013.01); *B01D 29/055* (2013.01); *B01D 29/085* (2013.01);
(Continued)

(58) Field of Classification Search
CPC .......................... B01D 29/055; B01D 29/085
See application file for complete search history.

(56) References Cited

U.S. PATENT DOCUMENTS

| 4,036,698 A | 7/1977 | Bush et al. |
| 4,614,585 A | 9/1986 | Mehra et al. |

(Continued)

FOREIGN PATENT DOCUMENTS

| CN | 103201374 A | 7/2013 |
| EP | 0713087 A1 | 5/1996 |

(Continued)

OTHER PUBLICATIONS

"CyQUANT Direct Cell Proliferation Assay," Jul. 20, 2009, retrieved from Internet—URL:http://tools.invitrogen.com/contents/sfs/manuals/mp35011.pdf (retrieved on Aug. 1, 2013).
(Continued)

*Primary Examiner* — Jonathan M Hurst
(74) *Attorney, Agent, or Firm* — Goodwin Procter LLP

(57) ABSTRACT

The invention relates to a filtration system for use in a method of determining the presence and/or amount of cells, for example, viable cells, in a liquid sample, and to methods of using and manufacturing such a filtration system. The filtration system includes a cup with an upper portion and a ring portion, where the ring portion is separably coupled to the upper portion.

22 Claims, 27 Drawing Sheets

Related U.S. Application Data continuation of application No. PCT/US2014/063950, filed on Nov. 4, 2014.

(60) Provisional application No. 61/899,436, filed on Nov. 4, 2013.

(51) Int. Cl.

| | | |
|---|---|---|
| *B01D 29/05* | (2006.01) | |
| *C12M 1/00* | (2006.01) | |
| *C12M 1/26* | (2006.01) | |
| *B01D 63/08* | (2006.01) | |
| *B01D 65/02* | (2006.01) | |
| *B01D 69/06* | (2006.01) | |
| *B01D 69/12* | (2006.01) | |
| *G01N 1/31* | (2006.01) | |
| *G01N 1/40* | (2006.01) | |

(52) U.S. Cl.
CPC ......... *B01D 63/081* (2013.01); *B01D 63/087* (2013.01); *B01D 65/022* (2013.01); *B01D 69/06* (2013.01); *B01D 69/12* (2013.01); *C12M 33/14* (2013.01); *C12M 47/04* (2013.01); *G01N 1/31* (2013.01); *G01N 1/4077* (2013.01); *B01D 2311/2611* (2013.01); *B01D 2325/02* (2013.01); *B01D 2325/04* (2013.01); *B01D 2325/44* (2013.01); *G01N 2001/4088* (2013.01)

(56) References Cited

U.S. PATENT DOCUMENTS

| | | | |
|---|---|---|---|
| 5,308,483 | A | 5/1994 | Sklar et al. |
| 5,603,900 | A | 2/1997 | Clark et al. |
| 6,203,996 | B1 | 3/2001 | Duffy et al. |
| 6,459,805 | B1 | 10/2002 | Reynolds et al. |
| 7,582,483 | B2 | 9/2009 | Mizutani et al. |
| 8,441,634 | B2 | 5/2013 | Manian |
| 8,993,259 | B2 | 3/2015 | Stimpson |
| 8,993,260 | B2 | 3/2015 | Stimpson |
| 2005/0069973 | A1 | 3/2005 | Bashar et al. |
| 2006/0129327 | A1 | 6/2006 | Kim et al. |
| 2008/0305514 | A1 | 12/2008 | Alford et al. |
| 2010/0216183 | A1 | 8/2010 | Okanojo et al. |
| 2011/0294206 | A1 | 12/2011 | Tai et al. |
| 2012/0015394 | A1 | 1/2012 | Pflanz et al. |
| 2012/0104280 | A1 | 5/2012 | Manian |
| 2012/0107950 | A1 | 5/2012 | Manian |
| 2012/0114536 | A1 | 5/2012 | Manian et al. |
| 2013/0315802 | A1 | 11/2013 | Manian et al. |
| 2013/0316363 | A1 | 11/2013 | Wainwright et al. |
| 2013/0323745 | A1 | 12/2013 | Wainwright et al. |
| 2014/0319379 | A1 | 10/2014 | Manian |

FOREIGN PATENT DOCUMENTS

| | | |
|---|---|---|
| EP | 2305789 A1 | 4/2011 |
| WO | WO-1992/02632 A1 | 2/1992 |
| WO | WO-2000/019897 | 4/2000 |
| WO | WO-2003/022999 A2 | 3/2003 |
| WO | WO-2003/036290 A1 | 5/2003 |
| WO | WO-2010/006615 A2 | 1/2010 |
| WO | WO-2013/078409 A2 | 5/2013 |
| WO | WO-2013/166336 A1 | 11/2013 |
| WO | WO-2013/166337 A1 | 11/2013 |
| WO | WO-2013/166338 A2 | 11/2013 |
| WO | WO-2015/066721 A1 | 5/2015 |

OTHER PUBLICATIONS

AES Chemunex, ABRASP Meeting (Oct. 20, 2011), pp. 1-57, downloaded from http://www.abrasp.org.br/downloades/2011/aes.pdf on Apr. 9, 2014.

Anonymous (2007) "Invitrogen Bacteria Counting Kit," downloaded from https://tools.lifetechnologied.com/contents/sfs/manuals,mp07277.pdf on Jun. 10, 2014.

Berney et al. (2007) "Assessment and interpretation of Bacterial Viability by Using Live/Dead Baclight Kit in Combination With Flow Cytometry," Applied and Environmental Microbiology, 73(10): 3283-3290.

Edward, R. (2012) "Red/Far-Red Fluorescing DNA-Specific Anthraquiones for Nucl:Cyto Segmentation and Viability Reporting in Cell-Based Assays," Methods in Enzymology, 505:23-45.

Giao et al. (2009) "Validation of Syto9/Propidium Iodide Uptake for Rapid Detection of Viable But Noncultivable Legionella Pneumophila," Mcrobial Ecology, 58: 56-62.

International Search Report and Written Opinion for International Patent Aplication No. PCT/US2013/039347, dated Aug. 9, 2013 (9 pages).

International Search Report and Written Opinion for International Patent Aplication No. PCT/US2013/039349, dated Aug. 9, 2013 (8 pages).

International Search Report and Written Opinion for International Patent Aplication No. PCT/US2013/039350, dated Nov. 26, 2013 (9 pages).

International Search Report and Written Opinion for International Patent Aplication No. PCT/US2014/063950, dated Nov. 4, 2014 (10 pages).

Li et al. (2005) "A live-cell high-throughput screening assay for identification of fatty acid uptake inhibitors," Analytical Biochemistry, 336(1): 11-19.

Millipore ISOPORE Membrane Filters, downloaded from https://www.millipore.com/catalogue/module/c153 on Apr. 9, 2014.

Sterlitech PETE (Polyester) Membranes (2013), pp. 1-2, downloaded from http:/www.sterlitech.com/filters/membrane-disc-filters/polester-pete-membranes.html on Apr. 23, 2014.

Extended European Search Report issued for European application No. 14858814.8 dated May 4, 2017.

FILTRATION SYSTEM AND USE THEREOF

CROSS-REFERENCE TO RELATED APPLICATIONS

This application is a continuation of U.S. patent application Ser. No. 14/858,495, filed Sep. 18, 2015, which is a continuation of International Patent Application No. PCT/US2014/063950, filed Nov. 4, 2014, which claims priority to and the benefit of U.S. Provisional Patent Application No. 61/899,436, filed Nov. 4, 2013, the entire disclosures of each of which are incorporated herein by reference.

FIELD OF THE INVENTION

The invention relates generally to a filtration system for harvesting cells, for example, viable cells, in a liquid sample for later analysis, and to methods of using and manufacturing such a filtration system.

BACKGROUND

Microbial contamination by, for example, Gram positive bacteria, Gram negative bacteria, and fungi, for example, yeasts and molds, may cause severe illness and, in some cases, even death in human and animal subjects. Manufacturers in certain industries, for example, food, water, cosmetic, pharmaceutical, and medical device industries, must meet exacting standards to verify that their products do not contain levels of microbial contaminants that would otherwise compromise the health of a consumer or recipient. These industries require frequent, accurate, and sensitive testing for the presence of microbial contaminants to meet certain standards, for example, standards imposed by the United States Food and Drug Administration or Environmental Protection Agency.

Depending upon the situation, the ability to distinguish between viable and non-viable cells can also be important. For example, during the manufacture of pharmaceuticals and biologics, it is important that the water used in the manufacturing process is sterile and free of contaminants. Furthermore, it is important that water contained in medicines (for example, liquid pharmaceutical and biological dosage forms, for example, injectable dosage forms) and liquids (for example, saline) that are administered to a subject, for example, via non-parenteral routes, is also sterile and free of contaminants. On the other hand, the presence of some viable microorganisms in drinking water may be acceptable up to a point. In order to be potable, drinking water must meet exacting standards. Even though microorganisms may be present in the water supply, the water may still be acceptable for human consumption. However, once the cell count exceeds a threshold level, the water may no longer be considered safe for human consumption. Furthermore, the presence of certain predetermined levels of microorganisms in certain food products (for example, fresh produce) and drinks (for example, milk) may be acceptable. However, once those levels have been exceeded the food or drink may be considered to have spoiled and no longer be safe for human consumption.

Traditional cell culture methods for assessing the presence of microbial contamination and/or the extent of microbial contamination can take several days to perform, which can depend upon the organisms that are being tested for. During this period, the products in question (for example, the food, drink, or medical products) may be quarantined until the results are available and the product can be released. As a result, there is a need for systems and methods for rapidly detecting (for example, within hours or less) the presence and/or amount of microbial contaminants, in particular, viable microbial contaminants, in a sample. An important part of the process is capturing the cells to be analyzed, which must be completed in a quick, safe and consistent manner to enable the efficiency of the overall detection system and methods.

SUMMARY

The invention is based, in part, upon the discovery of an improved filtration system (also referred to herein as a cell capture system) that can be used with a cell detection system to determine the presence of viable cells in a cell containing sample. The filtration system can be used in combination with an optical detection system that detects the presence of cells, for example, viable cells in the sample. The results can be used to measure the bioburden (for example, to measure the number and/or percentage and/or fraction of viable cells) of a particular sample of interest.

The filtration system described herein provides a number of advantages over existing filtration systems. For example, the filtration system minimizes the risk of leakage of fluid sample around the membrane that captures cells thereby reducing the risk of inadvertently contaminating the portion of the filtration system that is touched or handled by the user or that is placed within a cell detection system. Furthermore, the filtration system is more user friendly than existing filtration systems as it requires a fewer manipulation steps during operation by a user, which can be advantageous given that each additional manipulation step has the potential to introduce contaminants into the sample being analyzed or the fluid sample being analyzed may inadvertently contaminate the user or the surrounding environment. This minimizes the risk of contaminating the user, the detection system, or the surrounding environment.

In one aspect, the invention provides a filtration system (cell capture system) for receiving a fluid sample. The system includes a cup having an upper portion and a ring with a periphery. The upper portion is separably coupled to the ring. The cup also includes a fluid permeable membrane attached to the periphery to produce a fluidic seal between the membrane and the ring. A portion of the membrane is adapted to retain cells thereon. The system also includes a base configured to receive the ring.

The membrane portion can (i) define a plurality of pores having an average diameter less than about 1 µm so as to permit fluid to traverse the second portion of the membrane while retaining cells thereon and (ii) be substantially non-autofluorescent when exposed to light having a wavelength in a range from about 350 nm to about 1000 nm. Moreover, the membrane portion may have a flatness tolerance of up to about 100 µm (i.e., within ±50 µm). In some embodiments, the cup is adapted to direct a fluid, when introduced into the upper portion, toward the membrane portion.

In certain embodiments, the ring is integrally formed with the upper portion of the cup. The ring can be separably coupled to the upper portion with a frangible connection, which can be a thin wall at an intersection of the upper portion and the ring. The frangible connection (e.g., a thin wall intersection) may define a circumferential groove. The frangible connection may also define a parting plane between the upper portion and the ring upon the application of a force sufficient to break the frangible connection. In other embodiments, the ring is separably coupled to the upper portion via at least one of a threaded connection, a bayonet connection, and an interference fit.

In some embodiments, the ring has a circumferential registration feature. The ring can include a plurality of protrusions about the periphery of the ring, and one of the plurality of protrusions has at least one of a width, a height, a thickness, and a spacing different than each of the other protrusions, which can act as a spatial register. In certain embodiments, the membrane is at least one of adhered, bonded, heat welded, and ultrasonically welded to the ring.

The base may include a cylindrical wall for receiving the ring. In certain embodiments, the cylindrical wall defines a plurality of notches that mate with a plurality of protrusions of the ring. One of the notches can be adapted to receive one of the plurality of protrusions having at least one of a width, a height, a thickness, and a spacing different than each of the other protrusions, which can facilitate spatial registration. The cylindrical wall can define a circumferential opening adapted to provide access to the ring, when the ring is disposed within the base, and can also define a recess adapted to receive a membrane support. The recess may define a plurality of openings adapted to permit the passage of fluid therethrough. In one embodiment, the base includes a registration feature, which may include a depression defined by a surface of the base.

The cup may further include at least one latch adapted to couple the cup to the base to provide the appropriate frictional interfit between the cup and the base so as to permit the appropriate level of torque to facilitate separation of the ring (with the associated membrane) from the upper portion of the cup but yet also permit subsequent removal of the ring (with the associated membrane) from the base. The latch may be adapted to resist separation of the cup and the base in a plane perpendicular to a parting plane, but not resist rotation of the cup relative to the base.

In another aspect, the invention provides a method of harvesting cells, if present in a fluid sample. The method includes introducing the fluid sample to the upper portion of the cup described above and permitting the fluid to pass through the membrane portion. In some embodiments, the method includes, after applying the fluid, separating the upper portion from the ring. Separating the upper portion from the ring can include applying a force sufficient to decouple the ring from the upper portion, which force may be applied by twisting the cup relative to the base. The method may also include, after applying the fluid, securing a plug to a bottom of the base.

In still another aspect, the invention provides a method of manufacturing the cell capture system described above. The method includes providing a ring with a periphery, securing a fluid permeable member to a periphery to produce a fluidic seal between the membrane and the ring, and positioning the ring having the membrane secured thereto within a base configured to receive the ring. In some embodiments, the method includes, prior to producing the fluidic seal, separably coupling the ring to the upper portion. The positioning step may include mating the cup with the base in a predetermined circumferential orientation. In one embodiment, prior to positioning the cup within the base, the method includes placing a porous support in a recess formed in the base.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Figure 1A:
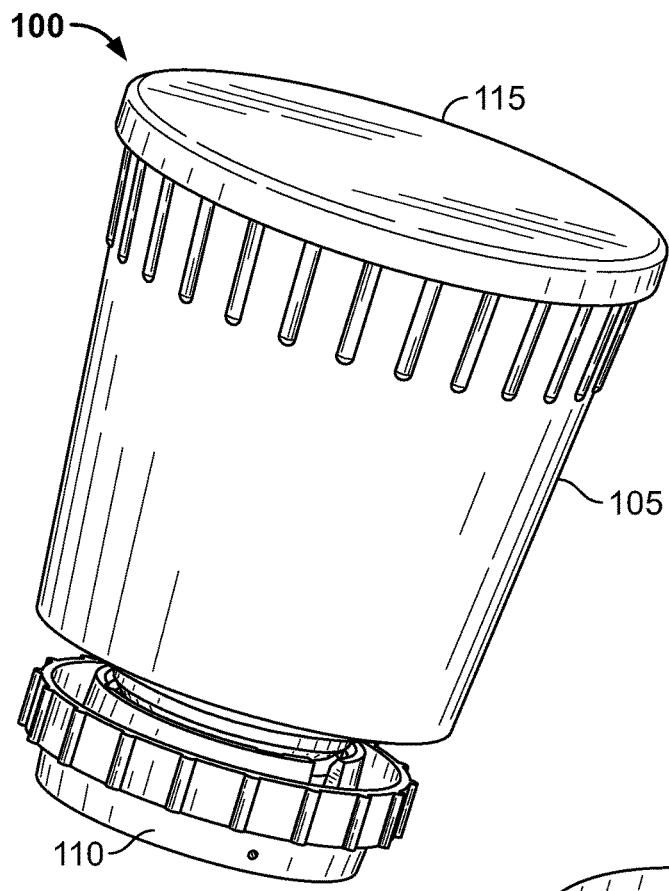
FIGS. 1A and 1B are schematic top and bottom perspective views, respectively, of an exemplary cell capture system.
Figure 1B:
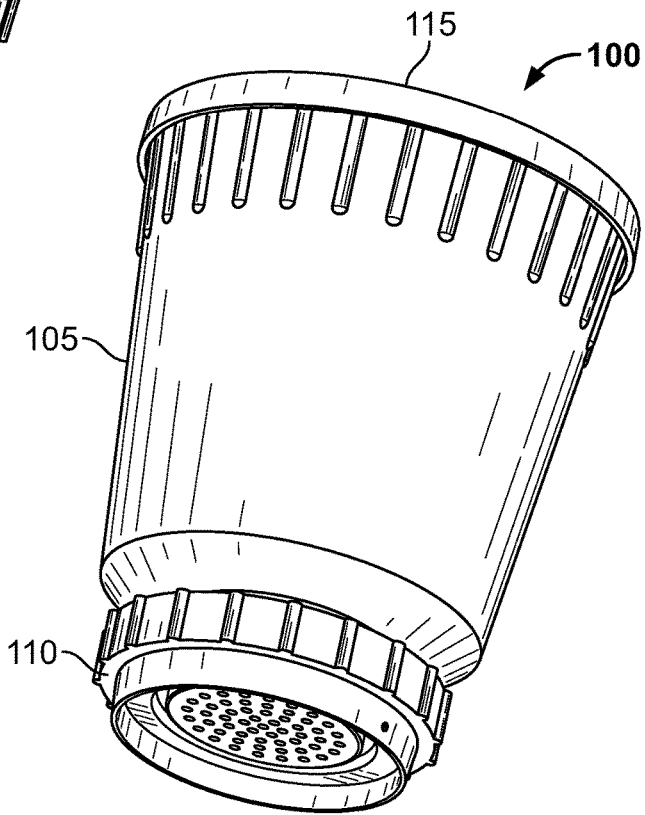
Figure 1C:
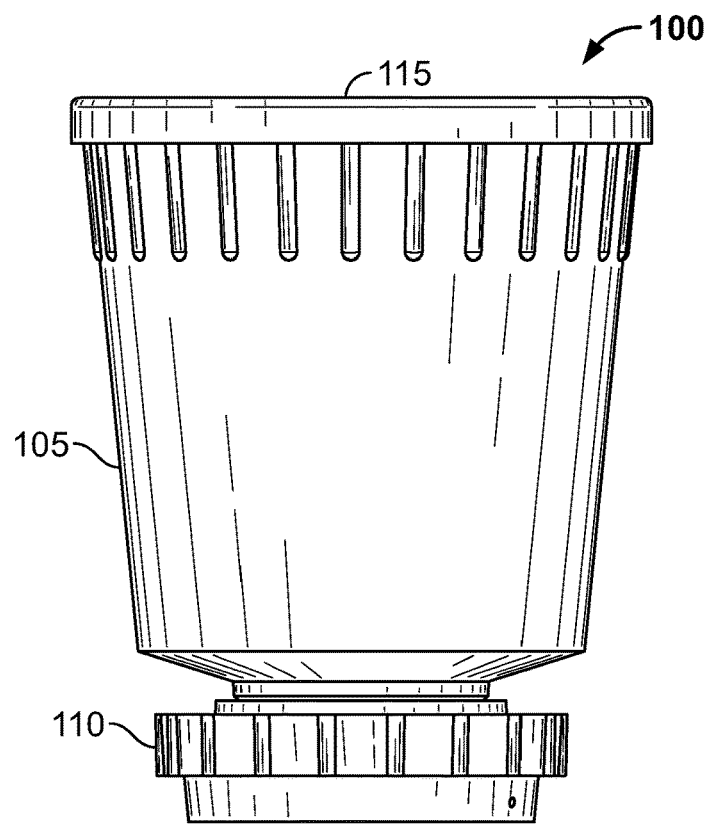
FIGS. 1C, 1D, and 1E are schematic side, top and bottom views of the exemplary cell capture system of FIGS. 1A and 1B.
Figure 1D:
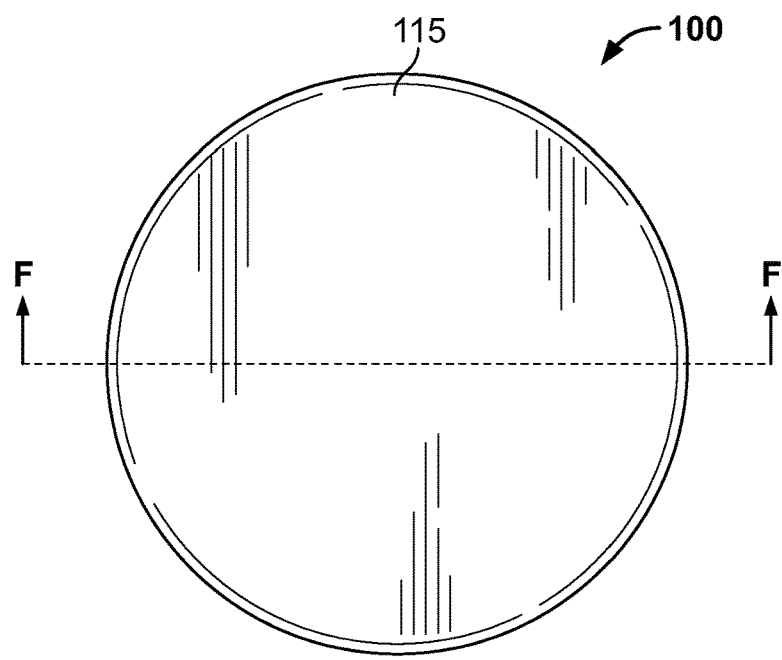
Figure 1E:
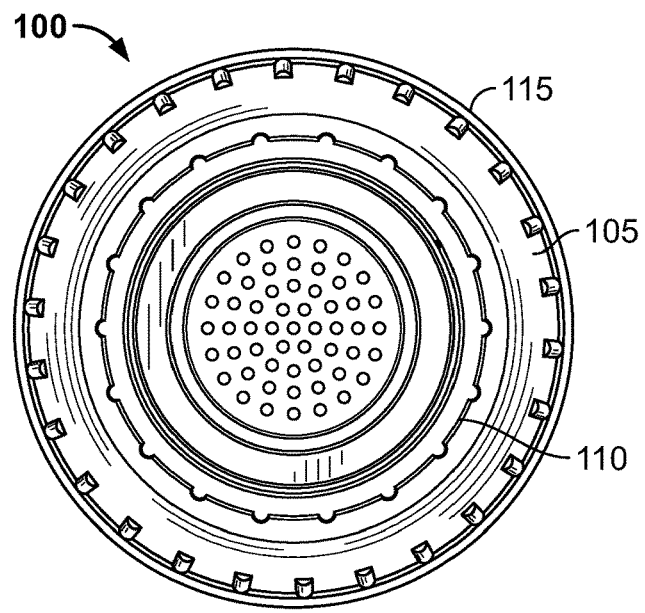
Figure 1F:
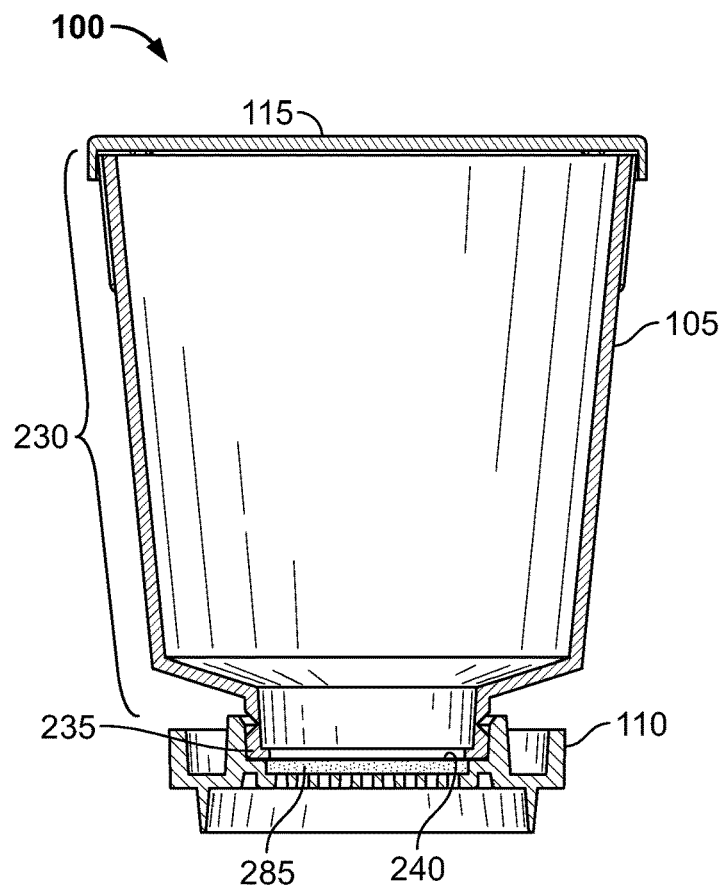
FIG. 1F is a schematic cross-section view of the exemplary cell capture system taken along line F-F of FIG. 1D.
Figure 2A:
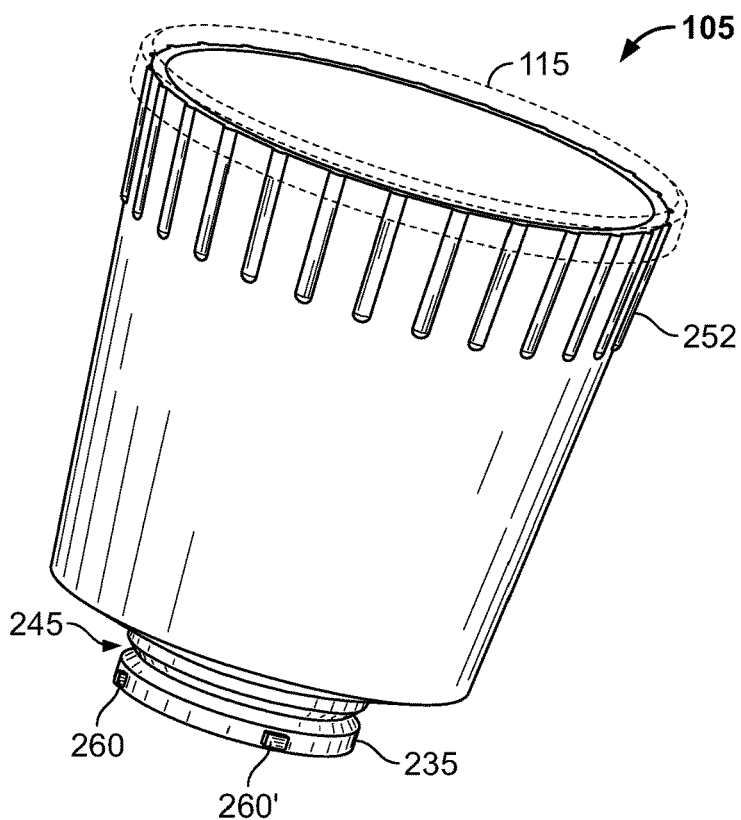
FIGS. 2A and 2B are schematic top and bottom perspective views, respectively, of an exemplary cup, which is part of the exemplary cell capture system of FIGS. 1A-1F.
Figure 2B:
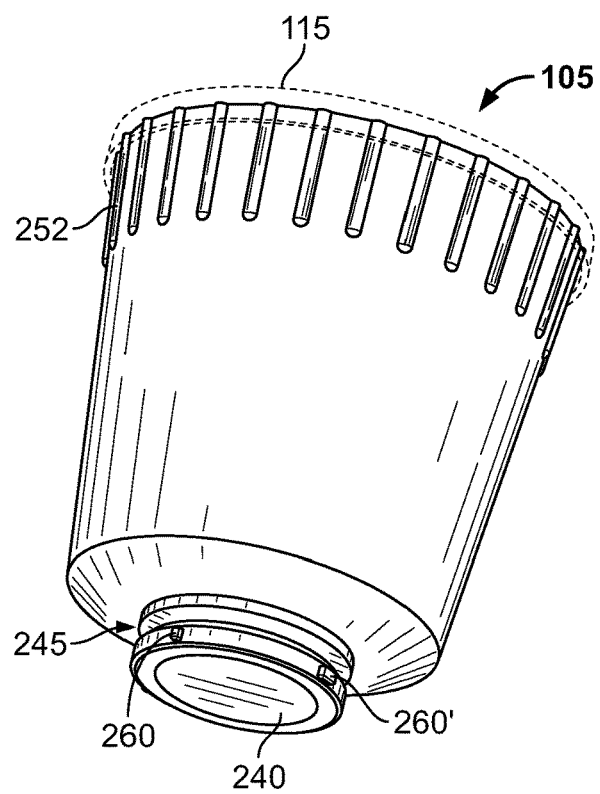
Figure 2C:
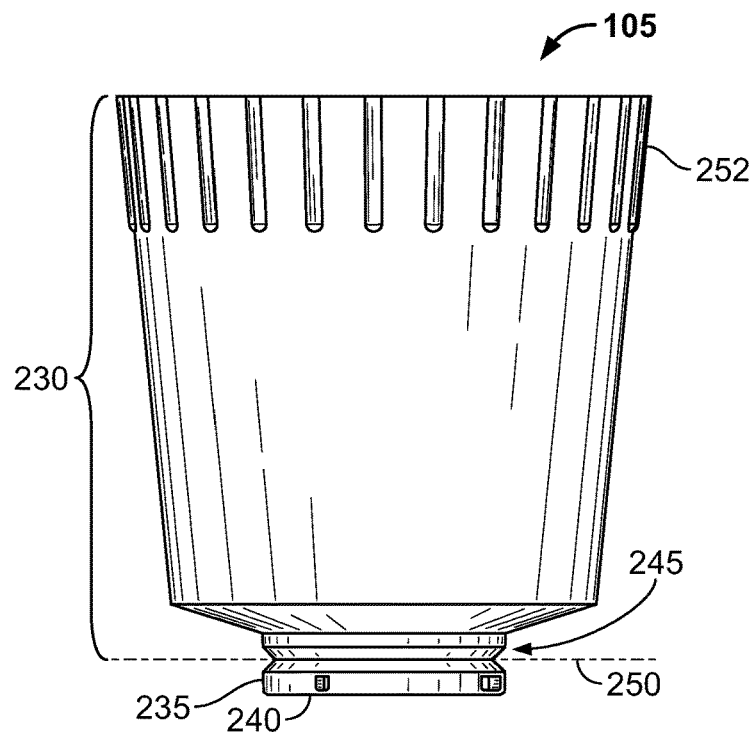
FIGS. 2C, 2D, and 2E are schematic side, top and bottom views of the exemplary cup of FIGS. 2A and 2B.
Figure 2D:
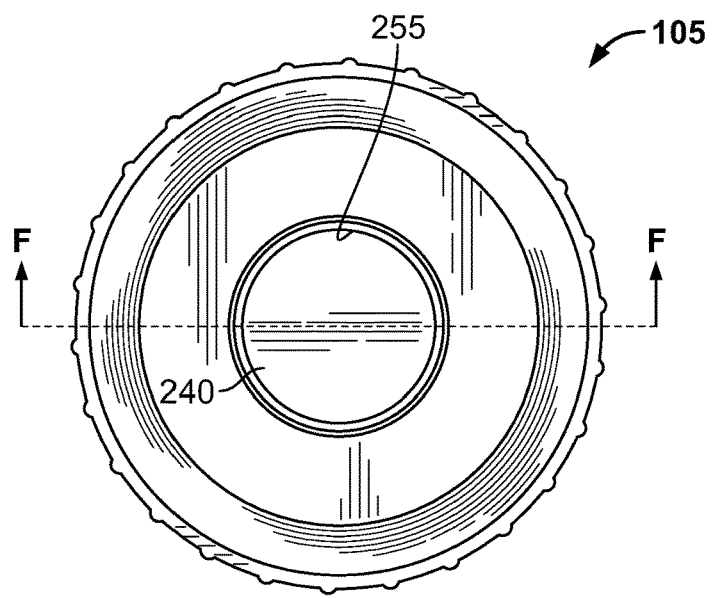
Figure 2E:
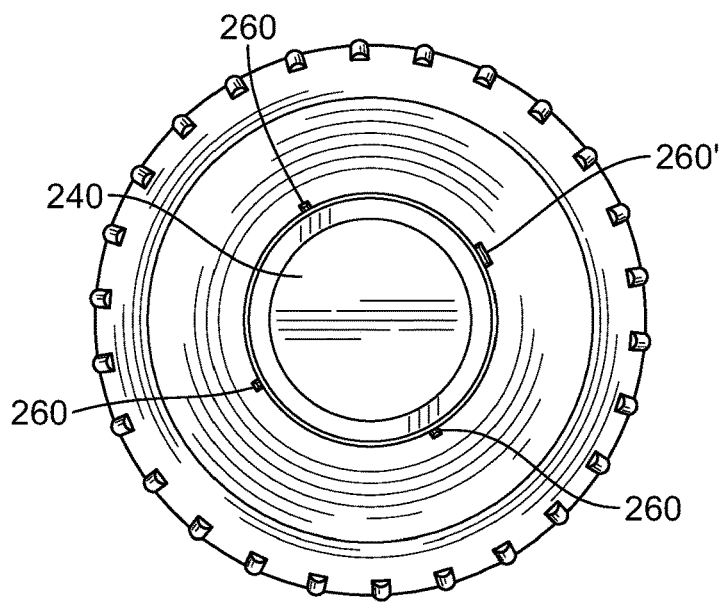
Figure 2F:
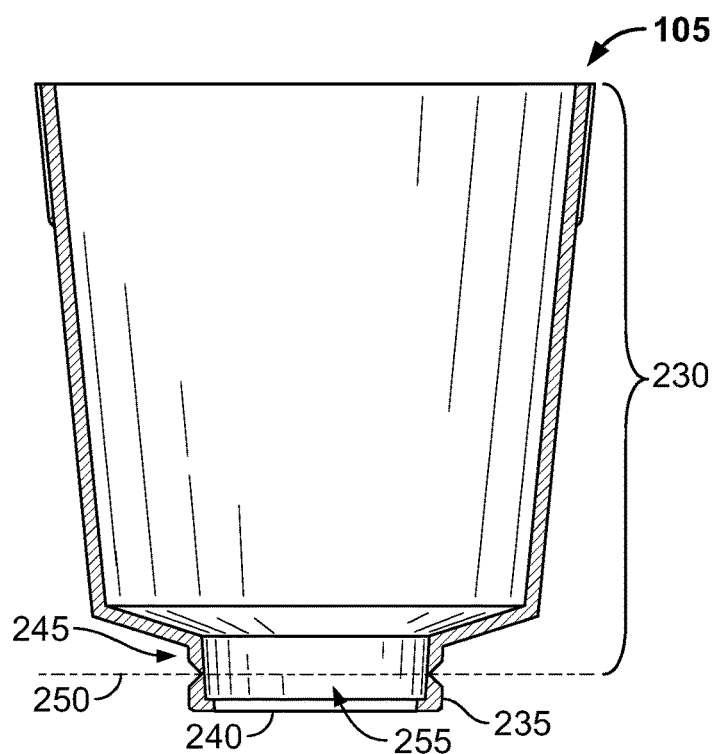
FIG. 2F is a schematic cross-section view of the exemplary cup taken along line F-F of FIG. 2D.
Figure 3A:
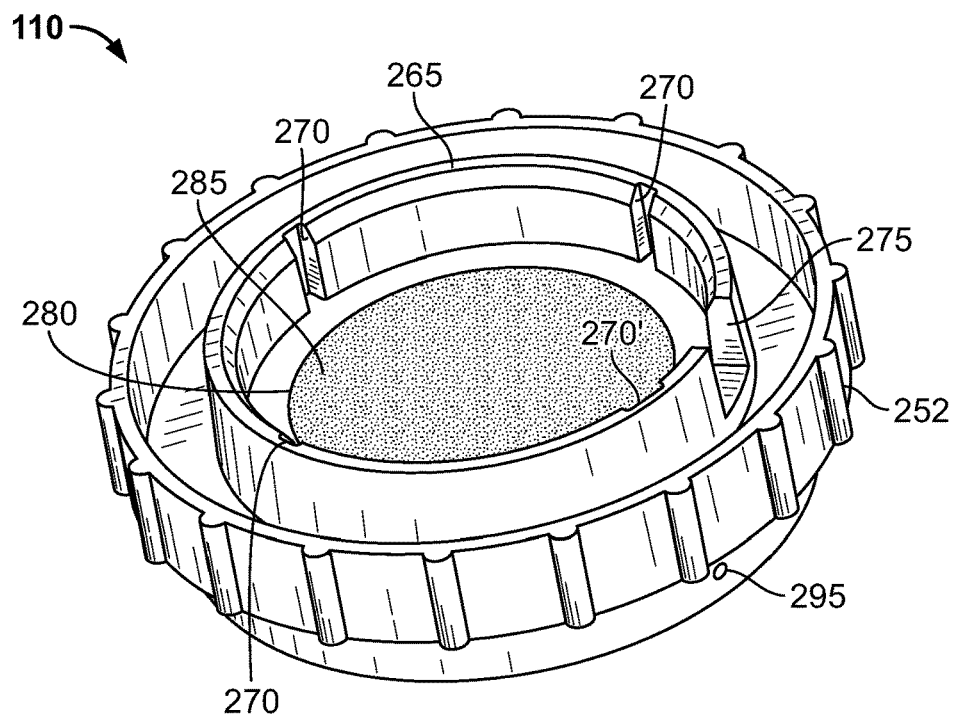
FIGS. 3A and 3B are schematic top and bottom perspective views, respectively, of an exemplary base, which is part of the exemplary cell capture system of FIGS. 1A-1F.
Figure 3B:
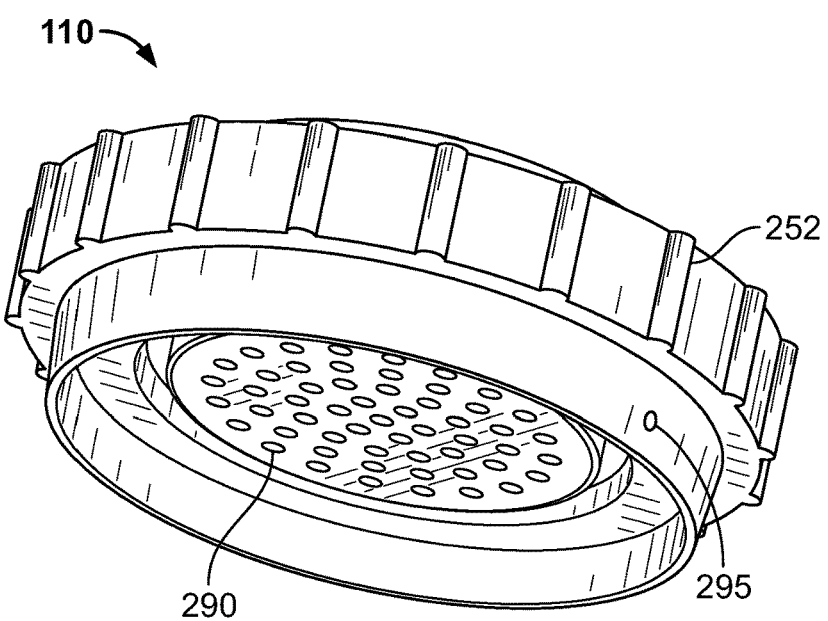
Figure 3C:
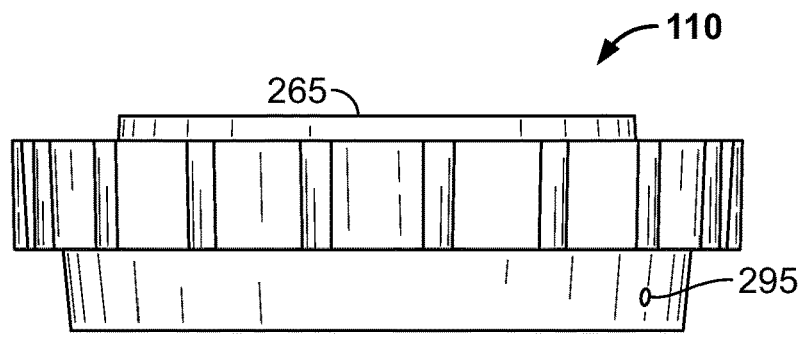
FIGS. 3C, 3D, and 3E are schematic side, top and bottom views of the exemplary base of FIGS. 3A and 3B.
Figure 3D:
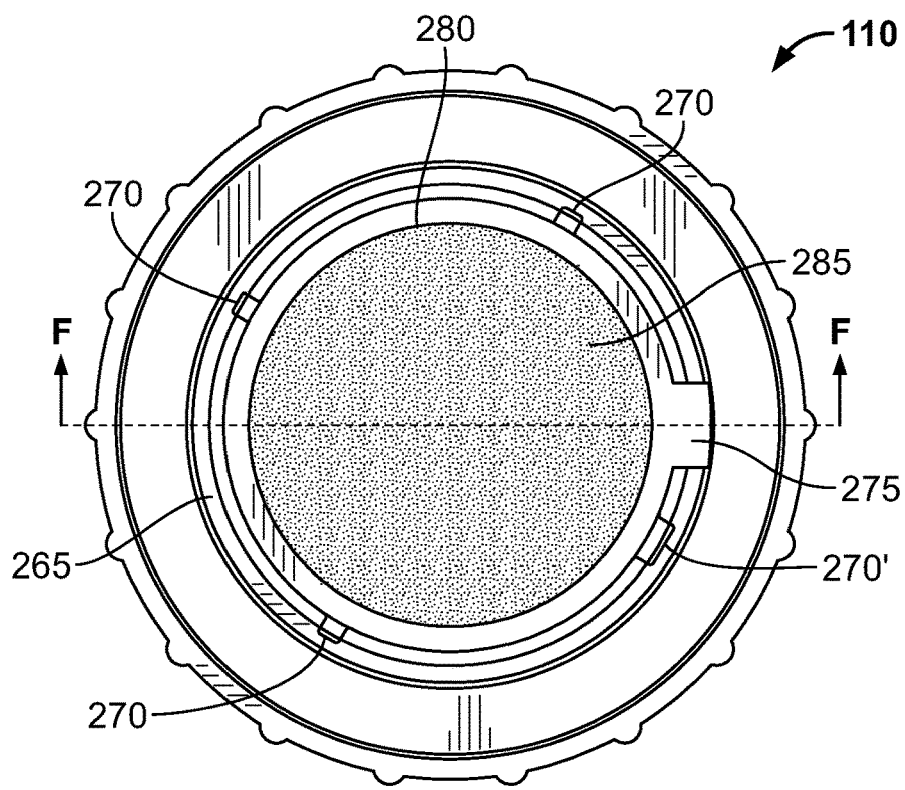
Figure 3E:
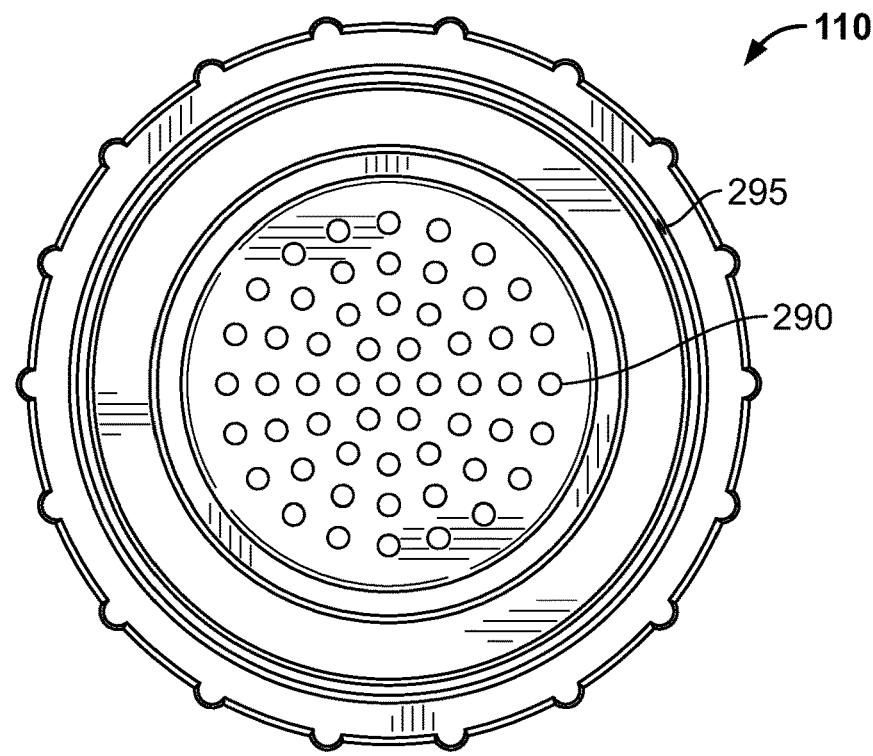
Figure 3F:
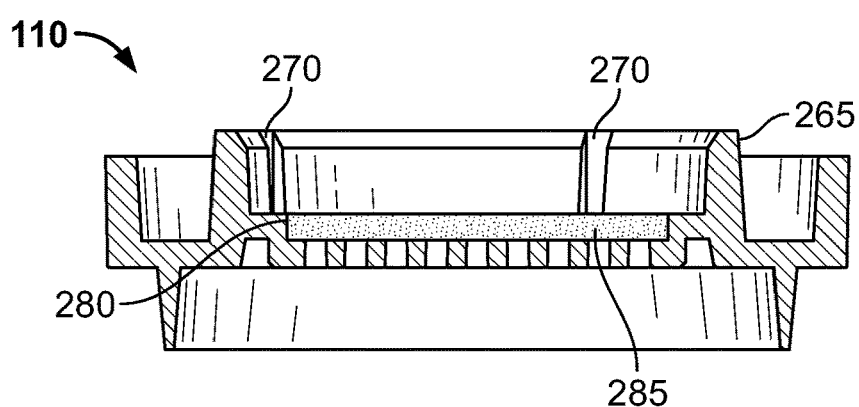
FIG. 3F is a schematic cross-section view of the exemplary base taken along line F-F of FIG. 3D.
Figure 4A:
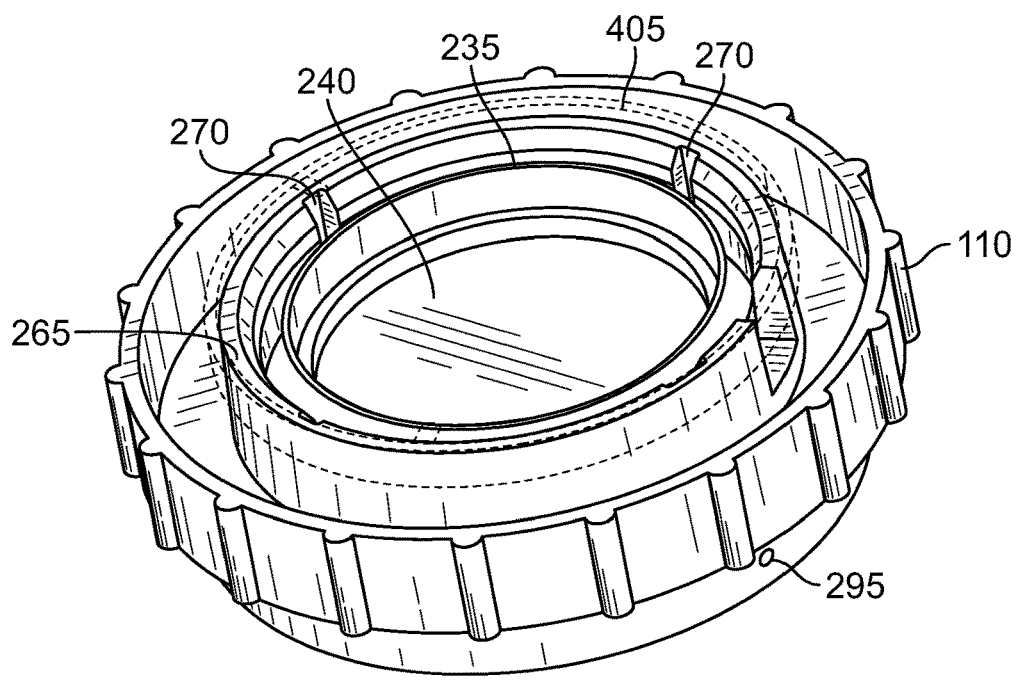
FIGS. 4A and 4B are schematic top and bottom perspective views, respectively, of an exemplary base assembly including the exemplary base of FIGS. 3A-3F.
Figure 4B:
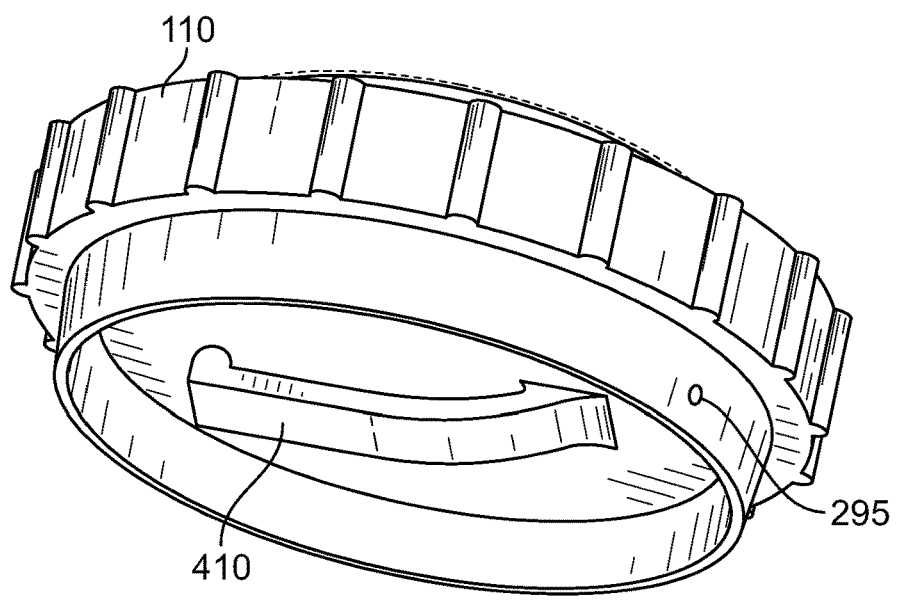
Figure 4C:
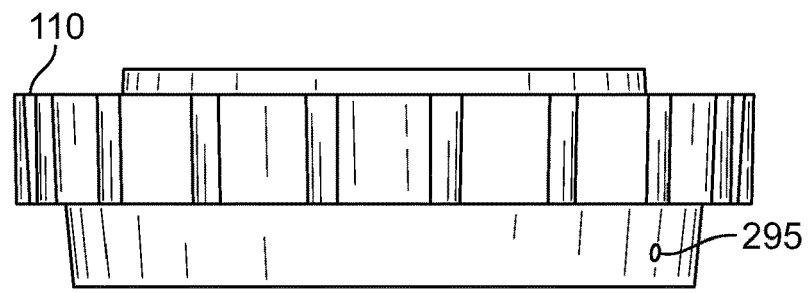
FIGS. 4C, 4D, and 4E are schematic side, top and bottom views of the exemplary base assembly of FIGS. 4A and 4B.
Figure 4D:
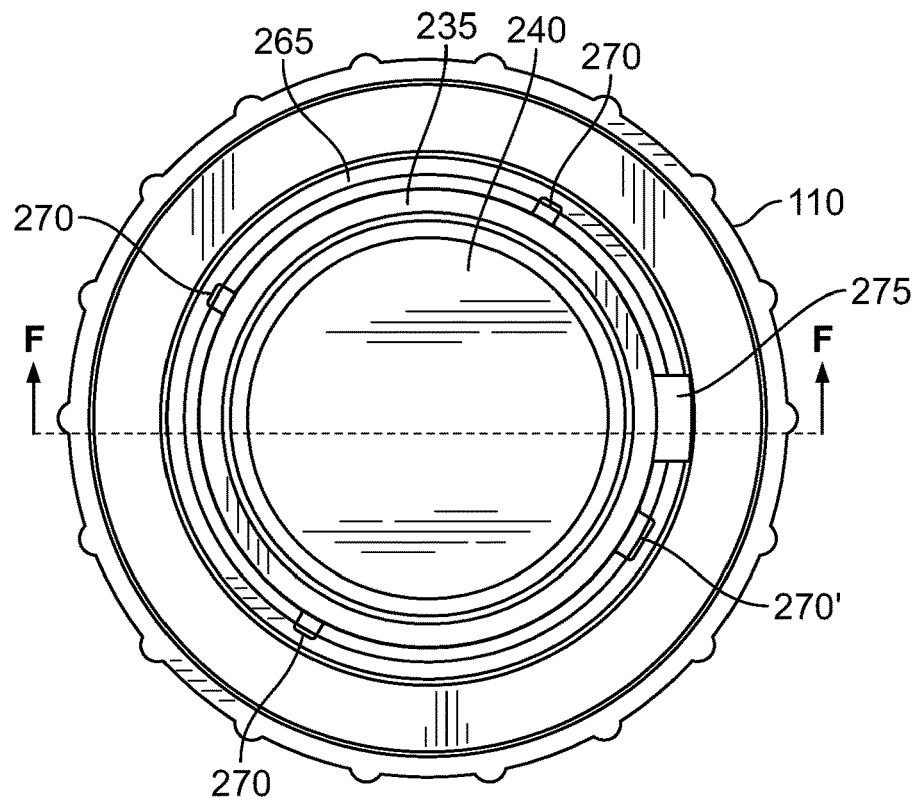
Figure 4E:
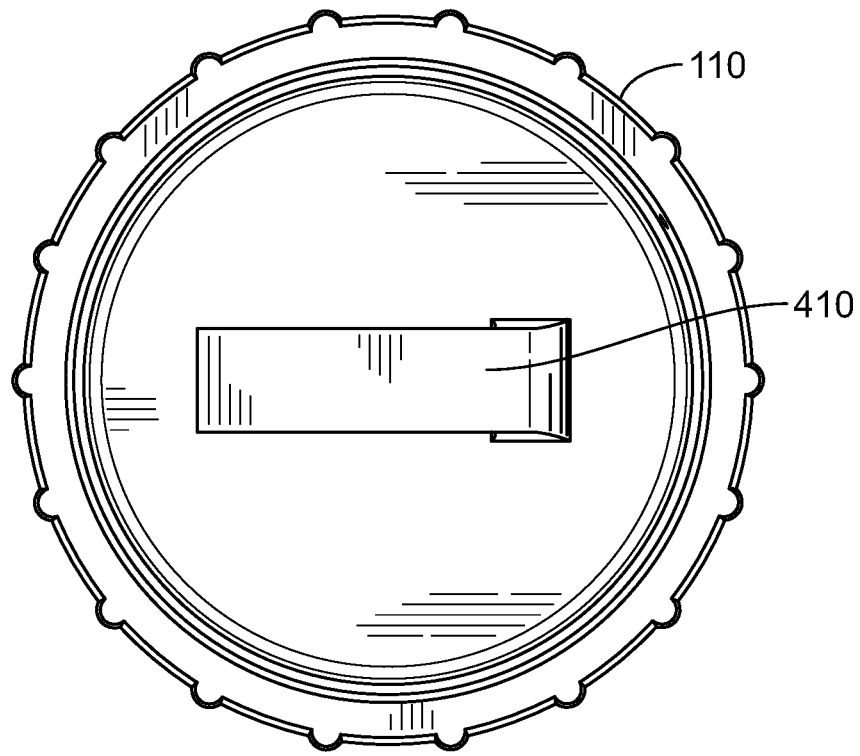
Figure 4F:
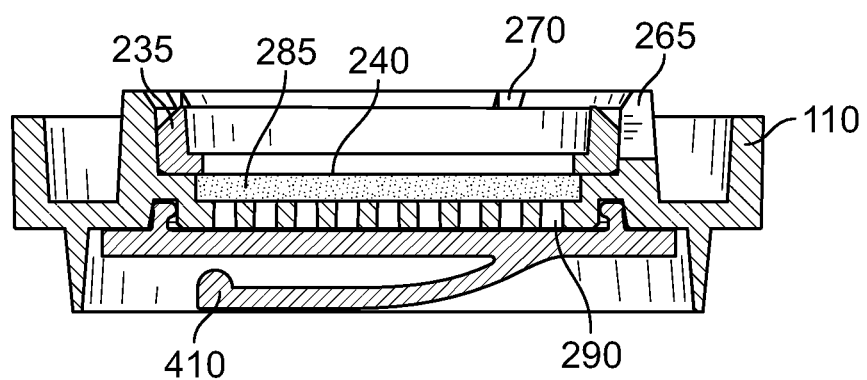
FIG. 4F is a schematic cross-section view of the exemplary base assembly taken along line F-F of FIG. 4D.

The instant invention is directed to a filtration system (cell capture system), a method of capturing/harvesting cells (including viable cells) in the filtration system, and a method for manufacturing the filtration system. The cell capture system and related methods can be used, either alone or in combination, to capture/harvest cells for later analysis, e.g., to determine the bioburden (e.g., to measure the number and/or percentage and/or fraction of viable cells in a sample) of a particular sample of interest.

The cell capture system can be used to capture cells (e.g., microbial cells, e.g., bacterial, yeast, or fungal cells) from a variety of sources, including from a liquid sample (e.g., a water sample), a comestible fluid (e.g., wine, beer, milk, baby formula or the like), a body fluid (e.g., blood, lymph, urine, cerebrospinal fluid or the like), growth media, a liquid sample produced by harvesting cells from a source of interest (e.g., via a swab) and then dispersing and/or suspending the harvested cells, and a liquid (e.g., buffer or growth media).

Each of the various aspects and certain embodiments of the invention will be discussed in detail below.

(I) Cell Capture System

The cell capture system described herein can be used with an optical detection system that detects the presence of viable cells. The results can be used to measure the bioburden (e.g., to measure the number and/or percentage and/or fraction of viable cells in a sample) of a particular sample of interest. Exemplary detection systems are described, for example, in International Patent Application No. PCT/IB2010/054965, filed Nov. 3, 2010, U.S. patent application Ser. No. 13/034,402, filed Feb. 24, 2011, International Patent Application No. PCT/IB2010/054966, filed Nov. 3, 2010, U.S. patent application Ser. No. 13/034,380, filed Feb. 24, 2011, International Patent Application No. PCT/IB2010/054967, filed Nov. 3, 2010, and U.S. patent application Ser. No. 13/034,515, filed Feb. 24, 2011.

The cell capture system described herein provides a number of advantages over existing cell capture systems. For example, the cell capture system described herein minimizes the risk of leakage of fluid sample around the membrane and, as a result, the fluid being characterized must pass through the membrane. This reduces the risk of inadvertently contaminating the portion of the cell capture system that is touched or handled by the user or that is placed within the detection system. Furthermore, the cell capture system described herein is more user friendly than other systems as it reduces the number of subsequent manipulation steps during operation by a user, which can be advantageous given that each additional manipulation step has the potential to introduce contaminants into the sample being analyzed or the fluid sample being analyzed may inadvertently contaminate the user or the surrounding environment. This minimizes contamination of the user or detection system or the surrounding environment. Furthermore, because the membrane is attached to a periphery of the ring, the membrane is substantially planar and can be created to have a flatness within a desired flatness tolerance necessary to keep the membrane within the focal plane of the detection system of certain optical detectors during operation.

One embodiment of a cell capture system 100, as shown schematically in FIGS. 1A-1F, includes a cup 105 and a base 110. A lid 115 to cover the cup 105 is optionally provided. The lid 115 can protect the inside of the cup 105 before use, such as during transport or preparation of a fluid to be applied. The cell capture system 100 may be shipped in the assembled, ready-to-use state, for example, as depicted in FIGS. 1A-1F, allowing a user to quickly capture or harvest cells without additional assembly, as described in greater detail below. The individual components of the cell capture system 100 are described in greater detail below.

The cup 105 comprises an upper portion 230, a ring 235, and a fluid permeable membrane 240, as depicted in FIGS. 1F and 2A-2F. The upper portion 230 is generally configured to direct fluid applied therein toward a lower portion of the cup 105 where the ring 235 and the membrane 240 are disposed. The ring 235 is separably coupled to the upper portion 230 so that, when desired, the ring 235 and the membrane 240 are retained while the upper portion 230 is disposed of separately. The ring 235 and associated membrane 240 can then be transferred to the optical detection system for analysis of the membrane.

In some embodiments, the upper portion 230 and the ring 235 are integrally formed together (e.g., through molding), with separability enabled through a frangible connection 245. The frangible connection 245 can take many forms, including a locally thinned wall section (e.g., a thickness of about 0.25 mm (0.0098 in.) instead of 1.5 mm (0.059 in.) for other parts of the cup 105) at an intersection of the upper portion 230 and the ring 235. The thinned wall section may resemble a groove at this intersection, and the frangible connection 245 may form a groove even if the wall section is not locally thinner. The frangible connection 245 defines a parting plane 250 (see, FIG. 2C), along which the upper portion 230 and the ring 235 are broken apart upon the application of a sufficient force (e.g., a torque of approximately 5-20 inch pounds (0.56-2.26 newton meters) or more). Grips 252 may be provided on the cup 105 and/or the base 110 to help the user apply the necessary force without slippage. The grips 252 can be a variety of forms, such as the depicted strips, or another surface feature which would increase grip for the user, such as raised spots. In other embodiments, the upper portion 230 and the ring 235 are formed separately, then later joined together through another connection, such as a threaded connection, a bayonet connection, and/or an interference fit.

In the depicted embodiment (see, FIG. 2F), the membrane 240 is connected, e.g., via heat welding or ultrasonic welding, to the ring 235 about a periphery of the ring that surrounds an opening 255. The membrane 240 may be otherwise adhered or bonded to the periphery of the ring 235, such as with a mechanical fastener or an adhesive. The connection may or may not be permanent. It is desirable to create a fluidic seal to restrict any fluid within the cup 105 from exiting or evacuating from the cup other than through the membrane 240. The planar membrane 240 has an exposed first surface (i.e., the side facing the interior of the ring 235), at least a portion of which is adapted to retain cells thereon. The membrane portion can: (i) define a plurality of pores having an average diameter less than about 1 µm so as to permit fluid to traverse the portion of the membrane while retaining cells thereon; and/or (ii) be substantially non auto-fluorescent when exposed to light having a wavelength in a range from about 350 nm to about 1000 nm. Optionally, the membrane portion also can have a flatness tolerance of up to about 100 μm. A flatness tolerance specifies a tolerance zone defined by two parallel planes within which the surface must lie. For example, in the embodiment described above having a flatness tolerance of up to about 100 μm, every point on the portion of the membrane 240 falls between two parallel planes spaced 100 μm apart.

The membrane 240 can be any of a variety of shapes, e.g., circular, annular, ovoid, square, rectangular, elliptical, etc., and can have some portion or all of one side exposed for cell retention. In one embodiment, the membrane 240 may be in the shape of a disc, e.g., a substantially planar disc. In certain embodiments, the portion of the porous membrane 240 for capturing cells and/or particles is greater than 400 mm$^2$, 500 mm$^2$, 600 mm$^2$, 700 mm$^2$, 800 mm$^2$, 900 mm$^2$ or 1,000 mm$^2$. In certain embodiments, the portion of the porous membrane 240 for capturing cells and/or particles is greater than 0.5 cm$^2$, for example, from 0.5 cm$^2$ to 300 cm$^2$, from 0.5 cm$^2$ to 100 cm$^2$, from 0.5 cm$^2$ to 50 cm$^2$, from 1 cm$^2$ to 300 cm$^2$, from 1 cm$^2$ to 100 cm$^2$, from 1 cm$^2$ to 50 cm$^2$, from 5 cm$^2$ to 300 cm$^2$, from 5 cm$^2$ to 100 cm$^2$, from 5 cm$^2$ to 50 cm$^2$. The membrane 240 (e.g., in the form of a disc) can have a thickness in a range selected from the group consisting of approximately from 1 μm to 3,000 μm, from 10 μm to 2,000 μm, and from 100 μm to 1,000 μm. In certain embodiments, the membrane may have a thickness of about 0.020".

The porous membrane 240 defines a plurality of pores having an average diameter less than about 1 μm so as to permit fluid to traverse the membrane 240 while retaining cells thereon. In certain embodiments, the average pore diameter is about or less than about 0.9 μm, 0.8 μm, 0.7 μm, 0.6 μm, 0.5 μm, 0.4 μm, 0.3 μm, 0.2 μm, 0.1 μm, or 0.05 μm. In certain embodiments, the average pore diameter is about 0.2 μm, and in other embodiments the average pore diameter is about 0.4 μm. Suitable membranes 240 can be fabricated from nylon, nitrocellulose, polycarbonate, polyacrylic acid, poly(methyl methacrylate) (PMMA), polyester, polysulfone, polytetrafluoroethylene (PTFE), polyethylene and aluminum oxide.

In addition, the porous membrane 240 is substantially non-autofluorescent when exposed to light having a wavelength in the range from about 350 nm to about 1,000 nm. As used herein with reference to the porous membrane 240, the term "substantially non-autofluorescent when exposed to a beam of light having a wavelength in the range from about 350 nm to about 1,000 nm" is understood to mean that the porous membrane 240 emits less fluorescence than a fluorescently labeled cell or a fluorescent particle disposed thereon when illuminated with a beam of light having a wavelength, fluence and irradiance sufficient to cause a fluorescence emission from the cell or particle. It is understood that a user and/or detector should be able to readily and reliably distinguish a fluorescent event resulting from a fluorescent particle or a fluorescently labeled cell from background fluorescence emanating from the porous membrane 240. The porous membrane 240 is chosen so that it is possible to detect or visualize a fluorescent particle or a fluorescently labeled cell disposed on such a porous membrane 240. In certain embodiments, the fluorescence emitted from a region of the porous membrane 240 (e.g., a region having approximately the same surface area as a cell or cell colony or particle being visualized) illuminated with a beam of light may be no greater than approximately 30% (e.g., less than 30%, less than 27.5%, less than 25%, less than 22.5%, less than 20%, less than 17.5%, less than 15%, less than 12.5%, less than 10%, less than 7.5%, less than 5%, or less than 2.5%) of the fluorescence emitted from a fluorescent particle or a fluorescently labeled cell, when measured under the same conditions, for example, using a beam of light with the same wavelength, fluence and/or irradiance.

Suitable membranes 240 that are non-autofluorescent can be fabricated from a membrane, e.g., a nylon, nitrocellulose, polycarbonate, polyacrylic acid, poly(methyl methacrylate) (PMMA), polyester, polysulfone, polytetrafluoroethylene (PTFE), or polyethylene membrane impregnated with carbon black or sputtered with an inert metal such as but not limited to gold, tin or titanium. Membranes 240 that have the appropriate pore size which are substantially non-autofluorescent include, for example, ISOPORE™ membranes (Merck Millipore), NUCLEOPORE™ Track-Etched membranes (Whatman), ipBLACK Track Etched Membranes (distributed by AR Brown, Pittsburgh, Pa.), and Polycarbonate (PCTE) membrane (Sterlitech).

In certain embodiments, the ring 235 has a circumferential registration feature to ensure proper positioning of the ring 235 in the base 110, and which also provides a consistent orientation for the membrane 240. Having a consistent orientation allows for reference to specific locations of cells on the membrane 240 (for example, the viable cells) retained on at least a portion of the membrane 240. For a disc shaped membrane, polar coordinates (i.e., radial "r" and angular "θ" coordinate locations) may be suitable. In some embodiments, the registration feature includes a plurality of protrusions 260 (see, FIGS. 2A and 2C), for example, at least two, three, four, five, six, seven, eight, nine, or ten protrusions spaced about the periphery of the ring 235. In one embodiment, the ring defines at least four protrusions. To properly orient the ring 235, and thereby the membrane 240, one of the protrusions 260' may be different than the other protrusions, such as having a different width, height, thickness, and/or spacing (e.g., spaced 60 degrees from another protrusion 260 instead of 90 degrees). A corresponding feature on the base (see below for more detail) is similarly sized to receive the protrusions 260, including the unique protrusion 260', so that the ring 235 and the base 110 may only be coupled in one orientation. The protrusions 260 can also be provided in a substantially symmetrical layout such that multiple orientations are possible.

The base 110, depicted in FIGS. 3A-3F, has a cylindrical wall 265 for receiving the ring 235. While cylindrical in the depicted embodiment, the wall 265 may be a variety of shapes complementary to the shape of the ring 235, such that the ring 235 could be received within the wall 265. The wall 265 defines a plurality of notches 270 sized and adapted to mate with the protrusions 260. A unique notch 270' can be sized or positioned to receive the unique protrusion 260', thereby achieving a consistent frame of reference. The protrusions 260 and the notches 270 are also dimensioned to provide sufficient frictional interfit so as maintain engagement when an appropriate torque is applied to ring 235/base 110 relative to the upper portion of the cup 230 at which point ring 235 breaks away from the upper portion of the cup 230 along parting plane 250. An overlap of approximately 0.787 mm (0.030 in.) may be sufficient, although greater, and lesser, overlaps can also work. The wall 265 also defines a circumferential opening 275 providing access to the ring 235 when it is disposed within the base 110 (as depicted in FIGS. 3A, 3D, 4A, and 4F). For example, depending upon the circumstances, a user can remove ring 235 together with membrane 240 by inserting an instrument, for example, forceps, through the opening 275, to remove the ring.

The base 110 further defines a recess 280 (see, FIG. 3F) for receiving a fluid permeable membrane support 285, that is optionally substantially planar. The membrane support 285 is permeable and adapted to contact a bottom surface of the membrane 240 when the ring 235 is disposed in the base 110. The fluid permeable support 285, for example, in the form of a smooth planar porous plastic frit, retains enough fluid to maintain moisture in the porous membrane 240 disposed adjacent the permeable support 285, which in certain embodiments, can be important to maintain the viability of cells retained on the porous membrane 240. The support 285 can have a thickness in a range selected from the group consisting of approximately from 0.1 mm to 10 mm, from 0.5 mm to 5 mm, and from 1 mm to 3 mm. The recess 280 defines openings 290 to permit the passage of fluid therethrough.

In order to facilitate accurate detection and count estimation of the captured cells, it is beneficial (even essential in some instances, depending on the configuration and capabilities of the detection system) that the membrane 240 is substantially planar (e.g., substantially wrinkle free) during cell detection. As used herein, the term "substantially planar" is understood to mean that an article has a flatness tolerance of less than approximately 100 μm (i.e., within +50 μm). This is because height imperfections (e.g., wrinkles) may interfere with the optical detection/measurement system, leading to erroneous results. As a result, it can be important for the porous membrane 240 when dry and/or wet and depending on detection conditions, retains a relatively tight flatness tolerance, within the detection capability of the detection system.

Under certain circumstances, depending upon the detection system employed, the membrane (and the cells disposed therein) is maintained within a tight flatness tolerance (e.g., within a flatness tolerance of up to about 100 μm (±50 μm), e.g., up to about 10 μm (±5 μm), up to about 20 μm (±10 μm), up to about 30 μm (±15 μm), up to about 40 μm (+20 μm), up to about 50 μm (±25 μm), up to about 60 μm (±30 μm), up to about 70 μm (±35 μm), up to about 80 μm (±40 μm), up to about 90 μm (±45 μm)), so that the cells can be visualized readily by a detection system within a narrow focal plane. If a dynamic focusing system is employed, it is contemplated that flatness tolerances greater than 100 μm can be tolerated. Accordingly, it can be preferable to use a support system that maintains the membrane and any captured cells in a substantially planar orientation and within a suitably tight flatness tolerance to permit reliable detection. Depending on the detection system and requirements post detection, the support system may be adapted to present and/or maintain planarity of the membrane when dry and/or when wet or moist after cells have been captured on the solid support after passing a cell containing solution through the solid support via pores disposed within the solid support.

Various approaches described below allow the porous membrane 240 to be held substantially flat after cells from a sample fluid are captured thereon and other approaches may be apparent to those skilled in the art based on the discussion herein.

In one embodiment, when the porous membrane 240 is wetted, surface tension between the membrane 240 and membrane support 285 conforms the bottom surface of the membrane 240 to an upper mating surface of the support 285. For example, in one embodiment, the membrane support 285 may be a fluid permeable, solid, substantially planar element that keeps the membrane 240 in a substantially planar configuration, for example, when the membrane 240 is wetted. The support 285 is porous, and the upper mating surface is substantially flat and smooth. In another embodiment, the support 285 is coated with a non-toxic adhesive, for example, polyisobutylene, polybutenes, butyl rubber, styrene block copolymers, silicone rubbers, acrylic copolymers, or some combination thereof. When a downward pressure is applied, for example, from a vacuum, the porous membrane 240 becomes loosely adhered to the support 285, which results in the porous membrane 240 conforming to the surface of the support 285. The support member 285 is porous, and the upper mating surface is substantially flat and smooth. For example, in one embodiment, the surface has a flatness tolerance of up to about 100 μm.

The diameter of the support 285 is approximately the same as the portion of the membrane 240 for receiving cells, and preferably the support 285 has a substantially uniform thickness. The support 285 can have a thickness in a range selected from the group consisting of approximately from 0.1 mm to 10 mm, from 0.5 mm to 5 mm, and from 1 mm to 3 mm. Materials suitable for making the porous support member 285 include plastic, polycarbonate, high density polyethylene (HDPE), glass, and metal. In one embodiment, the support member 285 is fabricated by sintering plastic particles made from poly (methyl methacrylate) having a mean diameter of 0.15-0.2 mm held at a temperature near the melting point of the particles and at a pressure sufficient to cause sintering of the particles to fuse them together and form a uniform structure.

Although the membrane 240 and the support 285 are depicted as circular, this is illustrative only. In other embodiments, the membrane 240 and/or the support 285 may be shaped as a square, a rectangle, an oval, etc. In general, the shape and the surface area of the support 285, if it is used, is selected such that the surface of the support 285 is approximately the same size as or slightly smaller than the portion of the membrane 240 for receiving cells disposed thereon.

The membrane 240 is disposed in contact with the substantially flat, smooth surface of the support member 285 before the sample fluid is poured onto the membrane 240. The generally flat surface helps keep the membrane 240 substantially flat after the sample fluid is drained. The support 285 can also serve as a reservoir for fluid passed through the membrane 240, to provide the additional benefit of preventing the membrane 240 and viable cells disposed thereon from drying out during the detection process. Drying can be detrimental to the viability of the cells retained on the membrane 240.

The base 110 also includes a register feature 295 to ensure proper and consistent positioning of the base 110 in a cell detection system. In one exemplary embodiment, register feature 295 is an indentation on an outer surface of the base 110. When the base 110 is inserted into a corresponding structure having a mating feature, e.g., a spring loaded ball bearing, a user will know the base is properly positioned when the base 110 "locks" into place, or some other feedback is provided to the user. Other registration techniques may be used, including those described above with respect to the interface between the ring 235 and the wall 265.

In another embodiment, a cell capture system 500 (as depicted in FIGS. 5A-5F) is largely similar to the cell capture system 100, including having similar components, such as a cup 505, a base 510, and a lid 515. The cell capture system 500 also includes a membrane 540 disposed on the bottom of the cup 505, which is designed to interface with a support member 585 to help maintain planarity of the membrane 540 (see, FIG. 5E). As the components of the cell capture system 500 share much in common with those of the cell capture system 100 (indicated through the use of common numbering), and have the same or similar properties as described above with respect to the cell capture system 100, only differences in various aspects of the components are described below.

As discussed with respect to cell capture system 100, protrusions 260 and the notches 270 are also dimensioned to provide sufficient frictional interfit so as maintain engagement when an appropriate torque is applied to ring 235/base 110 relative to the upper portion of the cup 230 at which point ring 235 breaks away from the upper portion of the cup 230 along parting plane 250. However, if the frictional interfit between ring 235 and base 110 is too great, it can be difficult to subsequently remove ring 235 from base 110 for subsequent analysis. The use of latches attached to the cup which interfit with the base 110 (see, FIGS. 5-7) can solve this problem. The latches permit the appropriate level of frictional interfit to break ring 235 from upper portion of the cup 230 but without requiring such friction to make it difficult for a user to separate ring 235 from base 110. These features are discussed in more detail with reference to FIGS. 5-7.

Figure 7A:
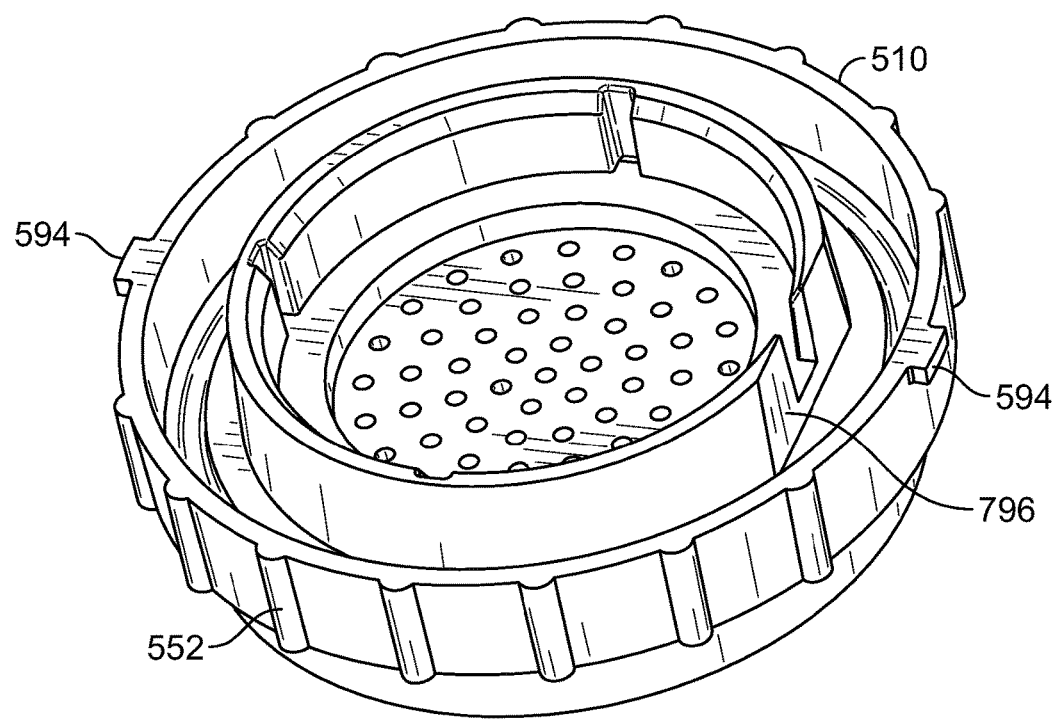
FIG. 7A is a schematic top perspective view of an exemplary base, which is part of the exemplary cell capture system of FIGS. 5A-5F.
Figure 7B:
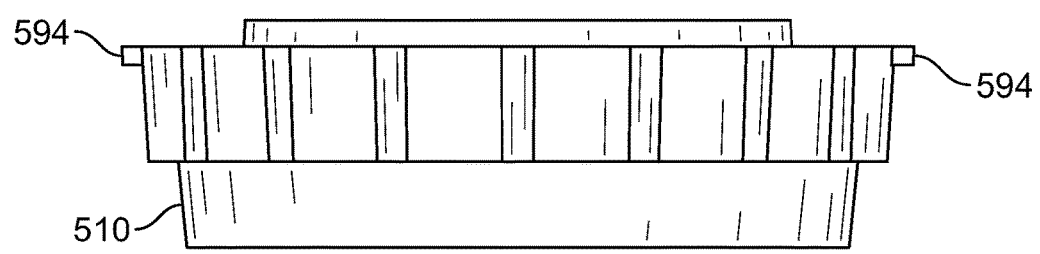
FIGS. 7B-7D are schematic side, top and bottom views, respectively, of the exemplary base of FIG. 7A.

Cup 505, depicted separately in FIGS. 5A, 5B, and 6A-6F, includes a plurality of latches 592 extending downward from an outer edge of the cup 505. The latches 592 are configured to engage corresponding protrusions 594 on the base 510 (see, FIGS. 7A and 7C) While two latches 592 are depicted, as few as one may be used, with an upper limit dictated solely by the size of the latches and the circumference of the surface on which the latches 592 are mounted. The latches 592 may be resilient, such that when the cup 505 is initially engaged with the base 510, the latches 592 flex around the ledges 594 before reengaging a lower portion of the ledges 594. As the latches 592 engage lower portions of the ledges 594, but not their sides, the latches 592 restrict longitudinal separation of the cup 505 from the base 510, but do not limit or increase the torque requirements to separate the cup 505 from the ring 535. As with the ring 135, the ring 535 has a differently dimension protrusion 660' in comparison to the other protrusions 660 to function as a registration feature. The protrusion 660' can be relatively long and extend into a space in the base 510 to allow for easier grasping (e.g., with forceps) during removal of the ring 535. This space for engaging the protrusion 660' may be even greater in embodiments where the base 510 has a flat surface 796 adjacent a circumferential opening 775, as depicted in FIGS. 7A and 7B. Grips 552 are shown on the outer surfaces of cup 505 and base 510 (see, FIG. 5F), which can help a user create the appropriate force or torque without slippage to separate ring 535 from the upper portion of cup 505.

The arrangement with the latches 592 can help increase the stability of the cell capture system 500 during transport, and limits the chances the cup 505 becomes disconnected from the base 510 at any time before desired use. Given the extra stability provided by the latches 592, the ring 535 may not be required to fit as snugly within the base 510 as in other embodiments. This can reduce the force required to remove the ring 535 from the base 510 after cell capture, reducing the likelihood the ring 535 becomes damaged or the membrane distorted, for example, outside the required flatness tolerance, during removal. Further, the addition of a longer protrusion 660' and in a wider space may aid a user by requiring less force to remove ring 535 from base 510.

Figure 5A:
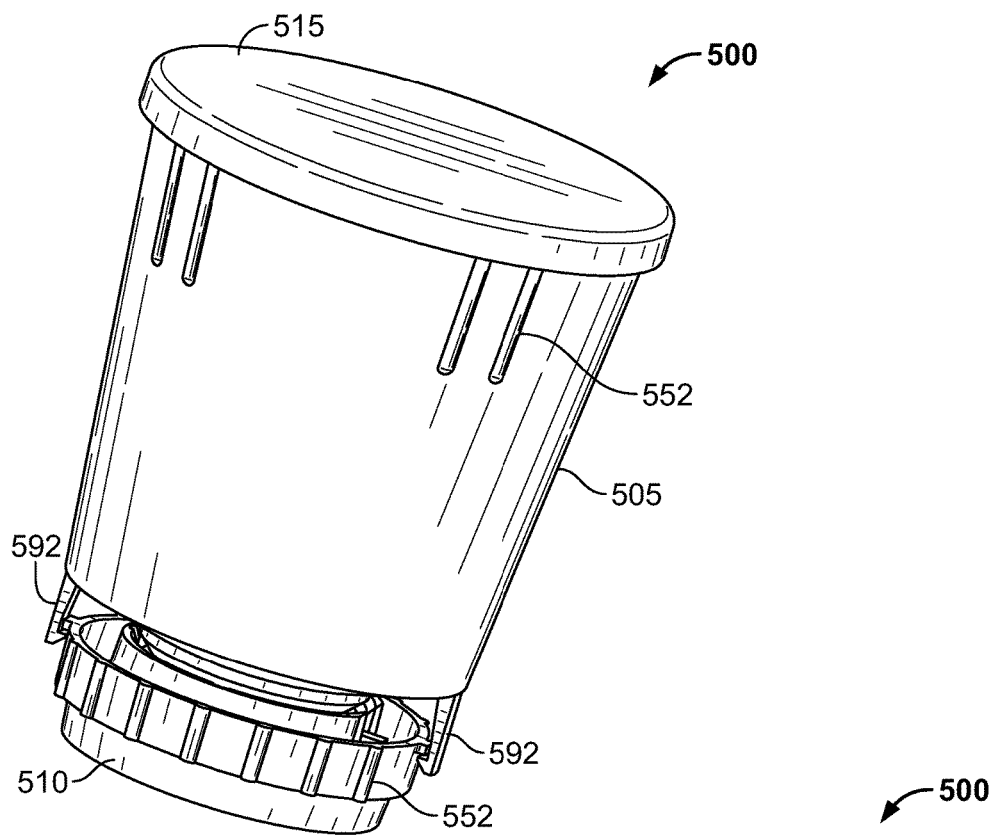
FIG. 5A is a schematic top perspective view of an exemplary cell capture system.
Figure 5B:
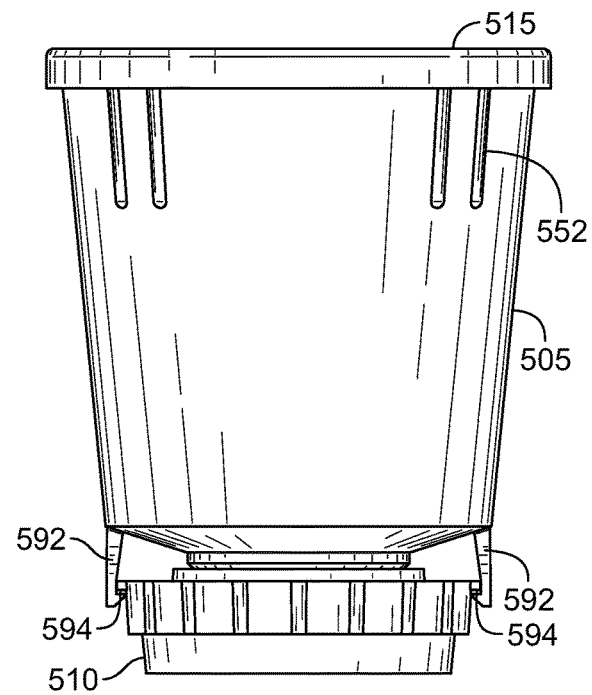
FIGS. 5B-5D are schematic side, top and bottom views, respectively, of the exemplary cell capture system of FIG. 5A.
Figure 5C:
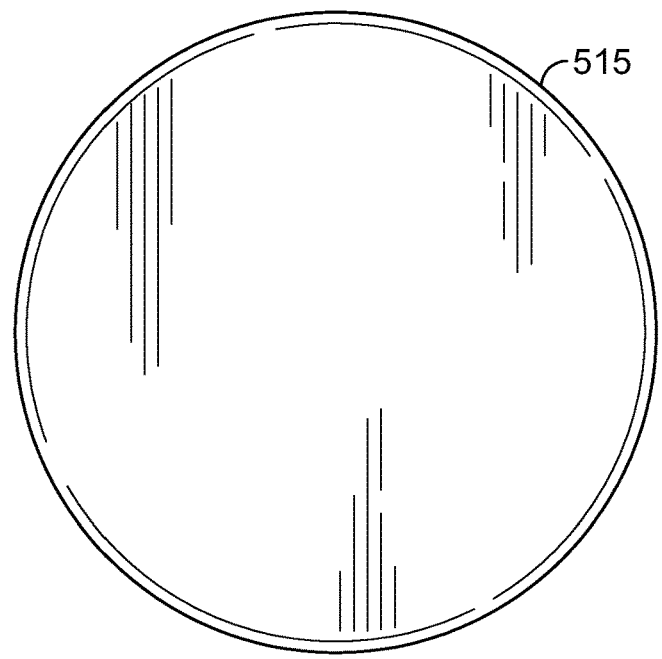
Figure 5D:
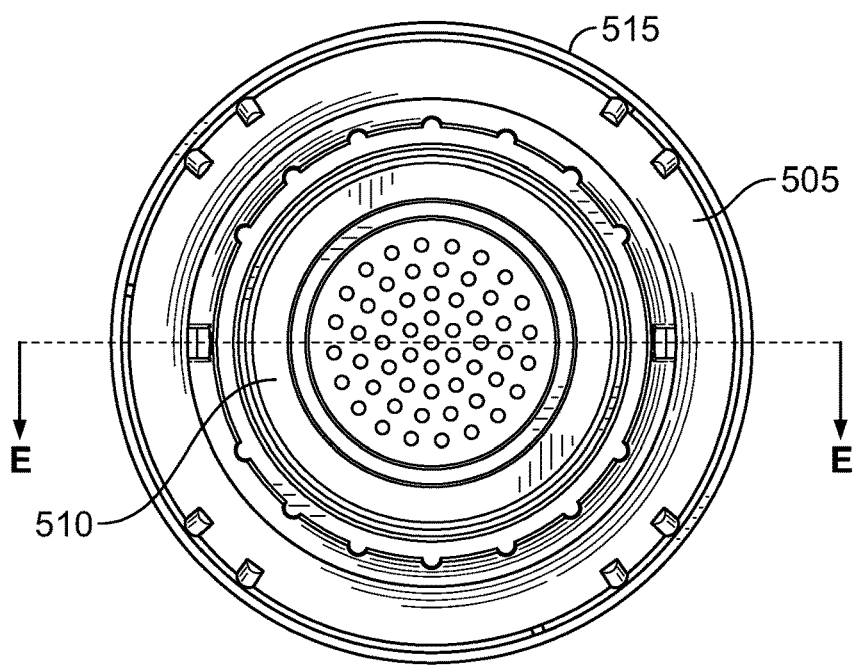
Figure 5E:
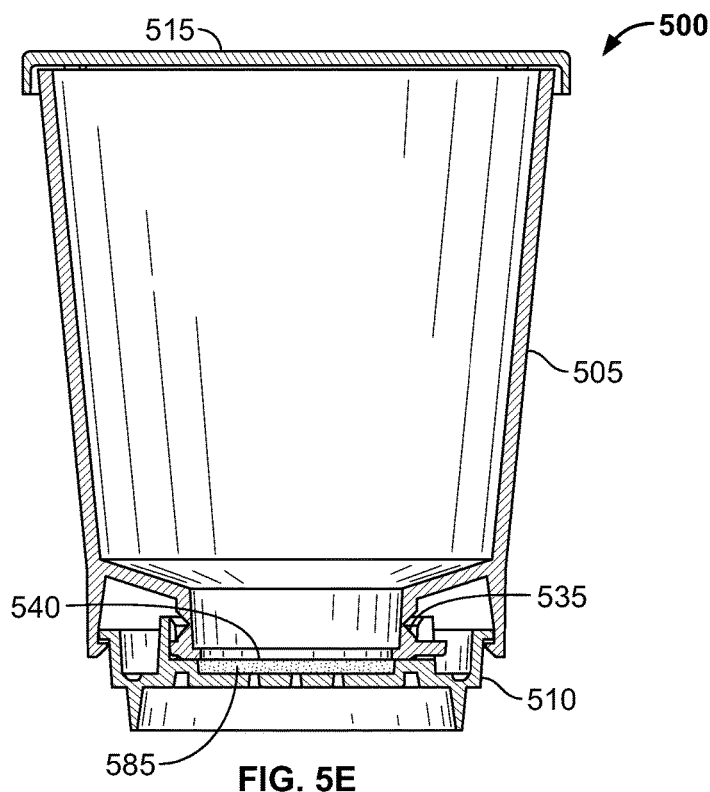
FIG. 5E is a schematic cross-section view of the exemplary cell capture system taken along line D-D of FIG. 1D.
Figure 5F:
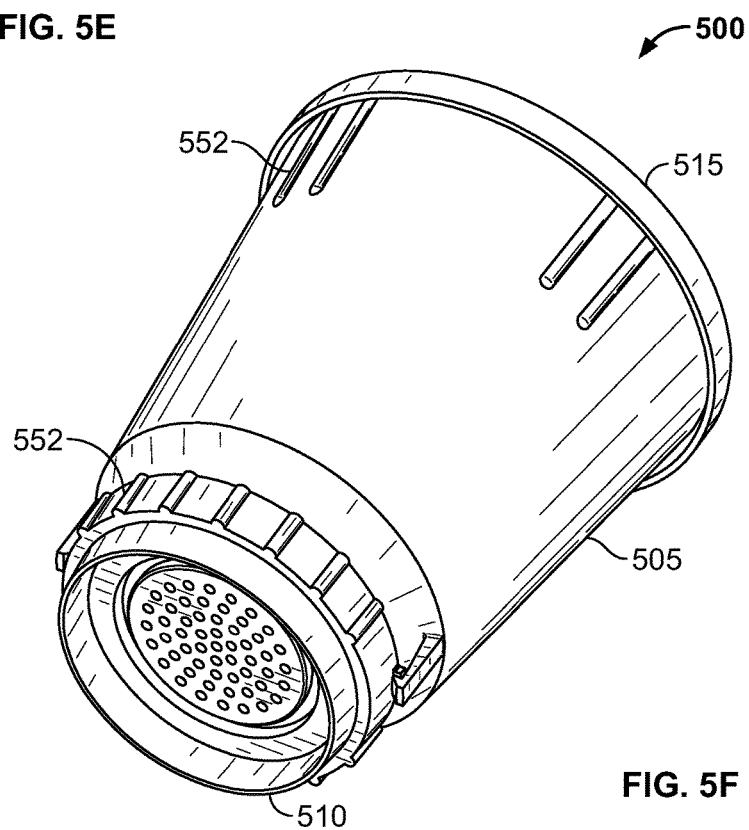
FIG. 5F is a schematic bottom perspective view of the exemplary cell capture system of FIG. 5A.
Figure 6A:
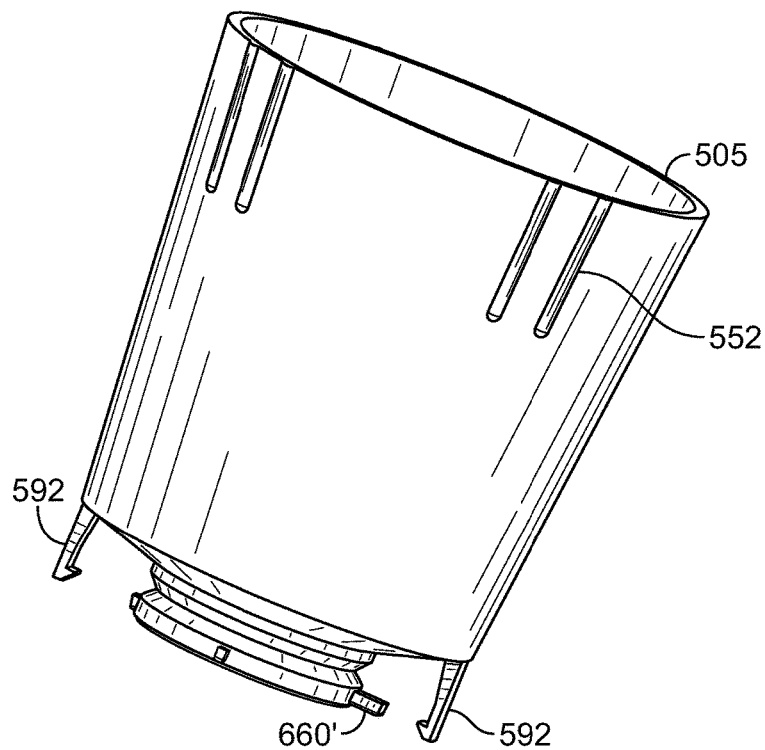
FIG. 6A is a schematic top perspective view of an exemplary cup, which is part of the exemplary cell capture system of FIGS. 5A-5F.
Figure 6B:
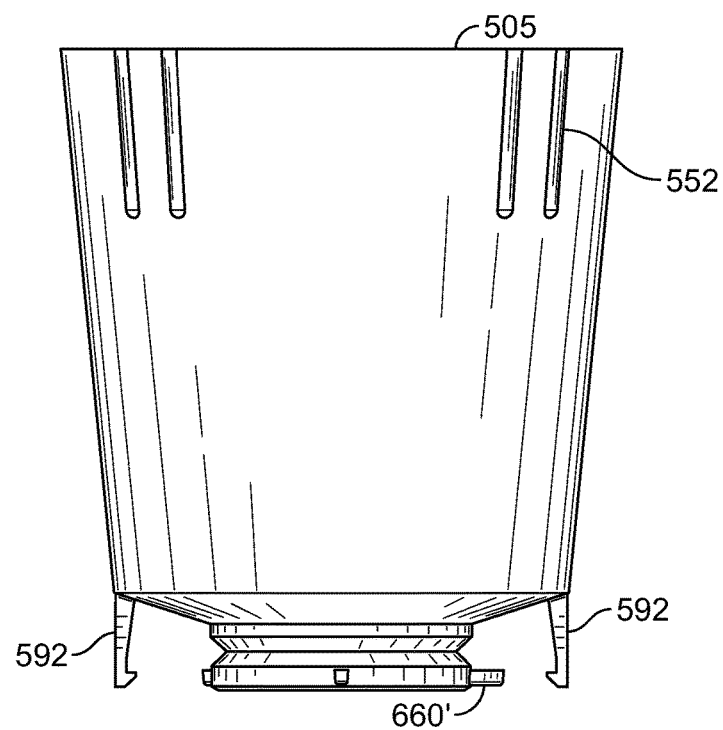
FIGS. 6B-6D are schematic side, top and bottom views, respectively, of the exemplary cup of FIG. 6A.
Figure 6C:
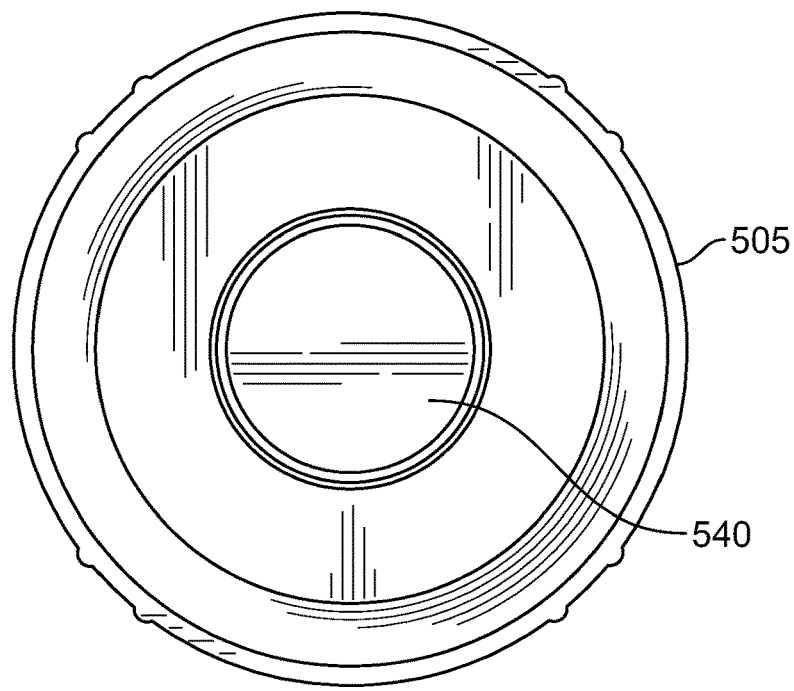
Figure 6D:
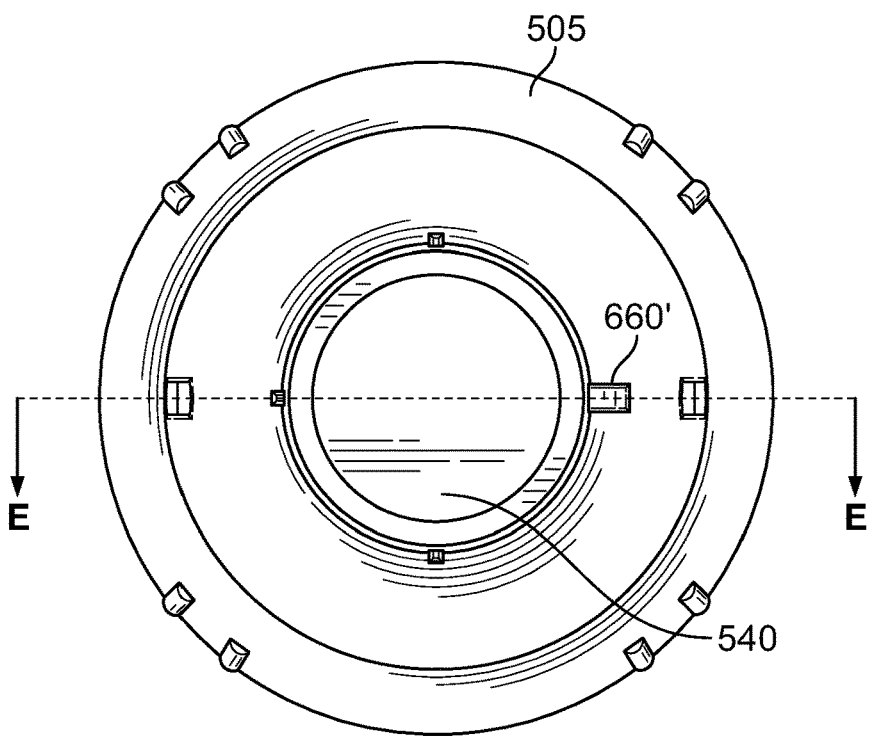
Figure 6E:
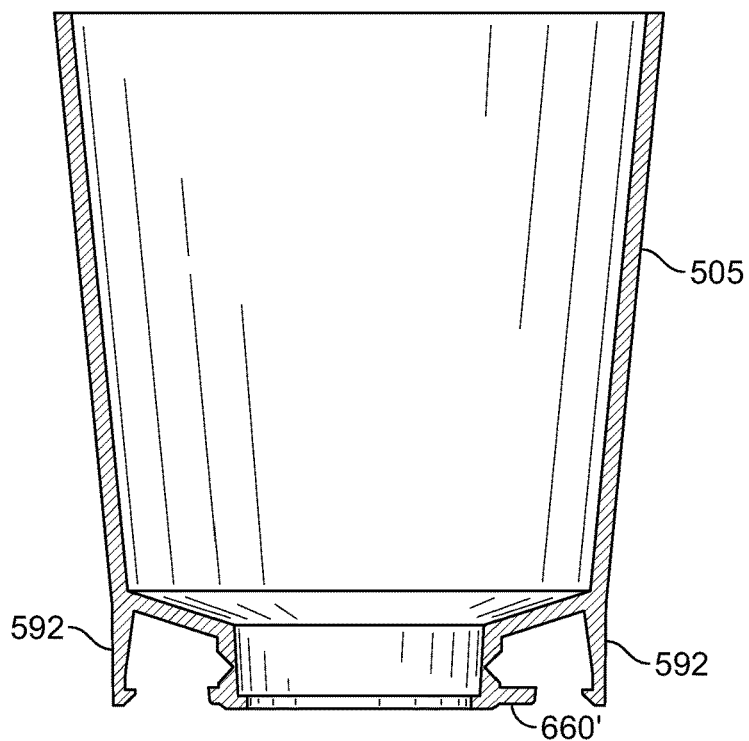
FIG. 6E is a schematic cross-section view of the exemplary cup taken along line D-D of FIG. 6D.
Figure 6F:
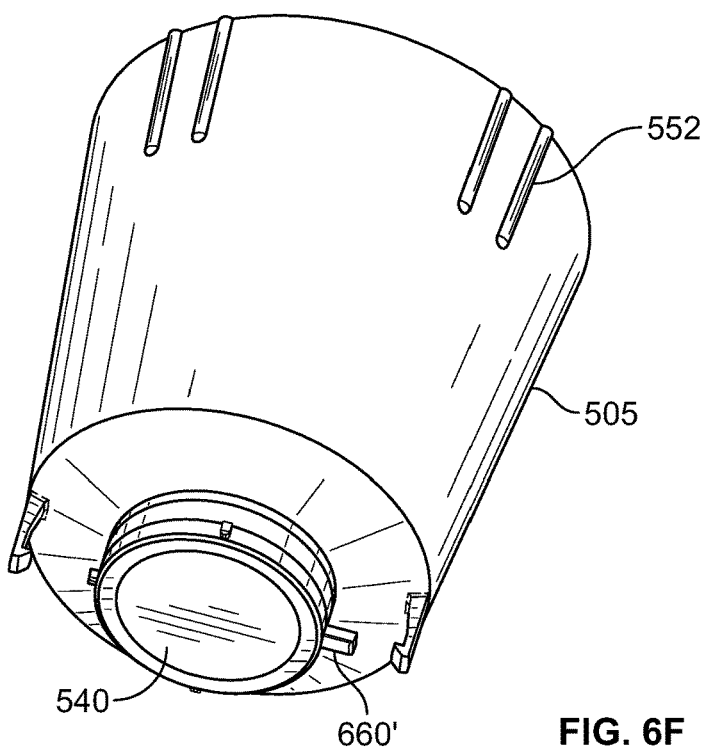
FIG. 6F is a schematic bottom perspective view of the exemplary cup of FIG. 6A.
Figure 7C:
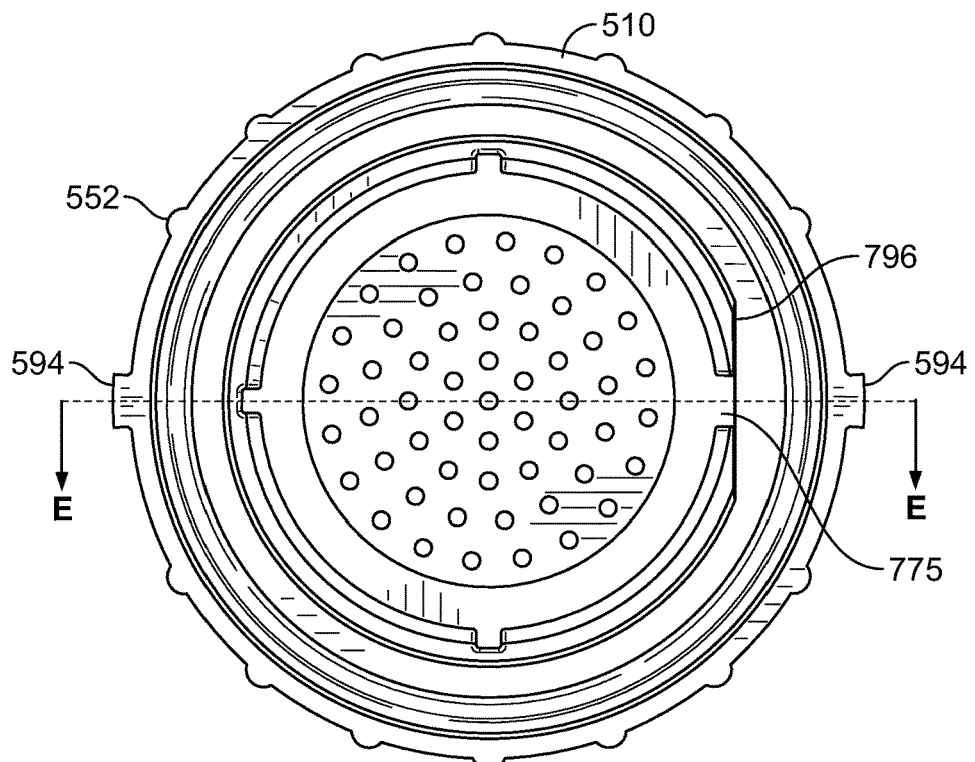
Figure 7D:
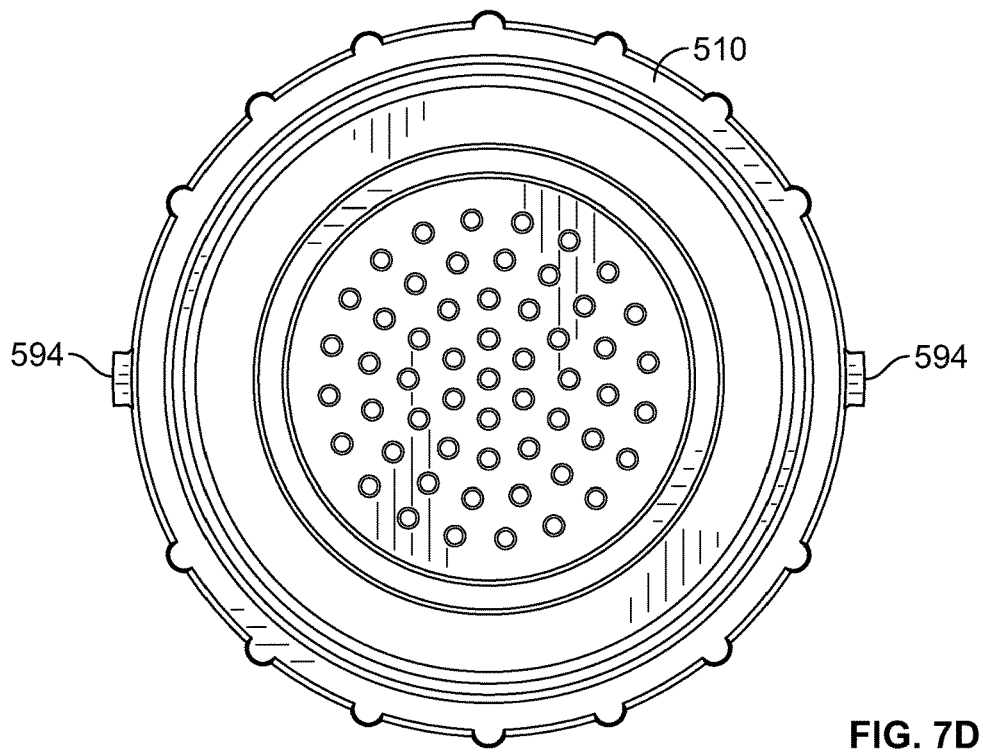
Figure 7E:
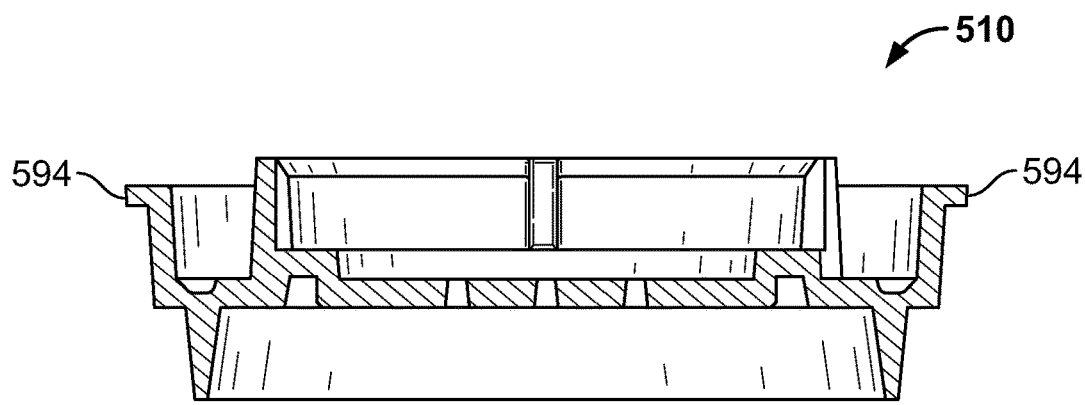
FIG. 7E is a schematic cross-section view of the exemplary base taken along line C-C of FIG. 7C.
Figure 7F:
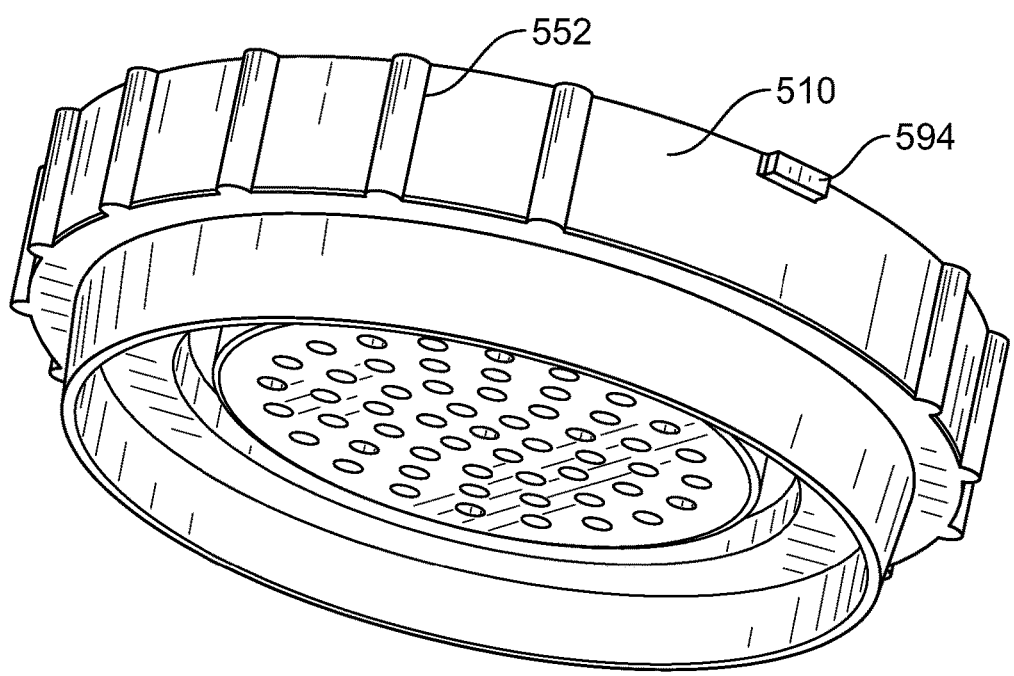
FIG. 7F is a schematic bottom perspective view of the exemplary base of FIG. 7A.
Figure 8A:
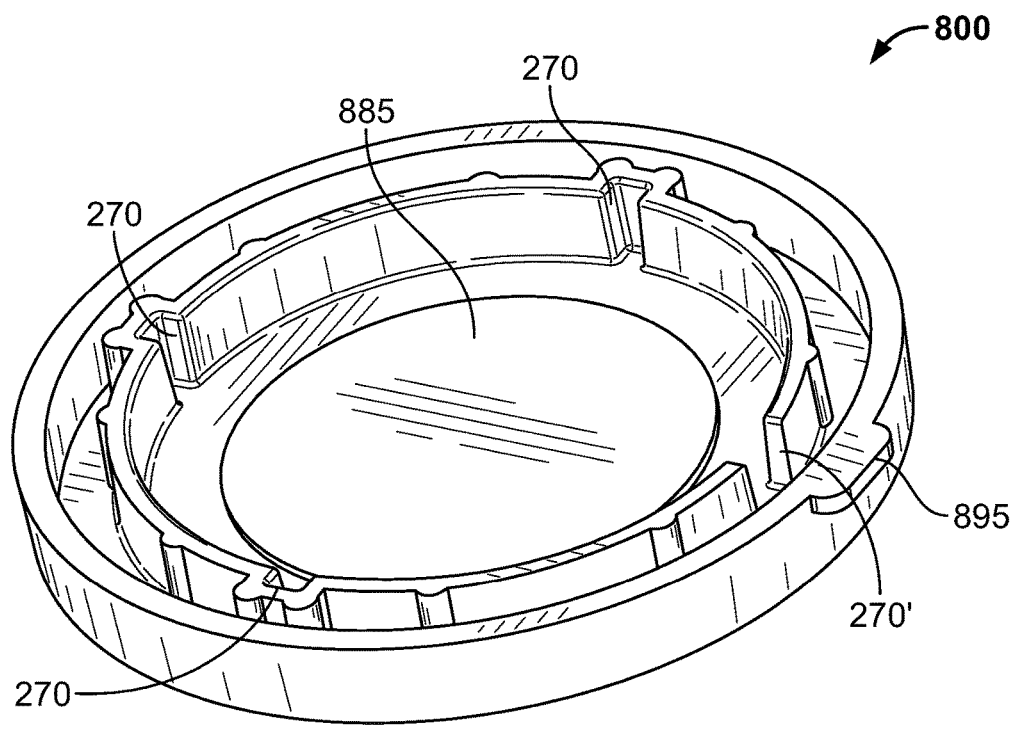
FIG. 8A is a schematic top perspective view of an exemplary adapter for use with a ring of a cup having a membrane.
Figure 8B:
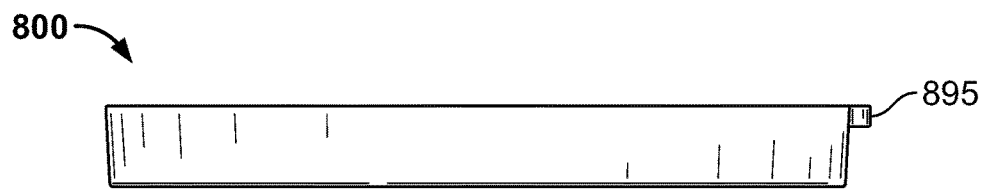
FIGS. 8B-8D are schematic side, top and bottom views, respectively, of the exemplary adaptor of FIG. 8A.
Figure 8C:
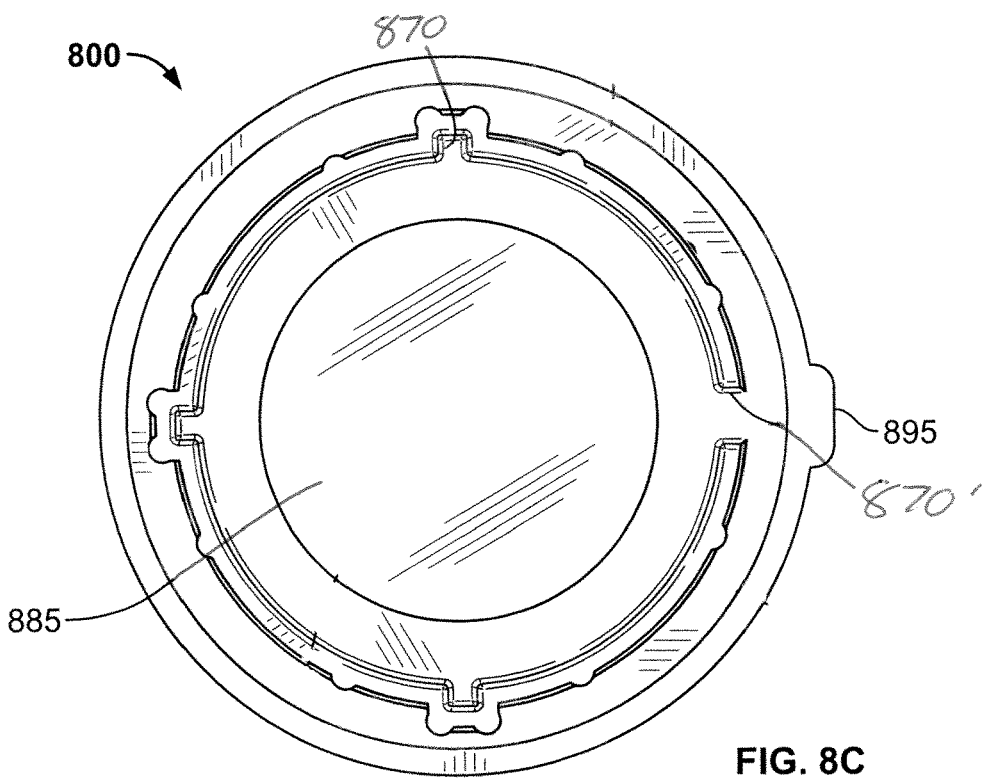
Figure 8D:
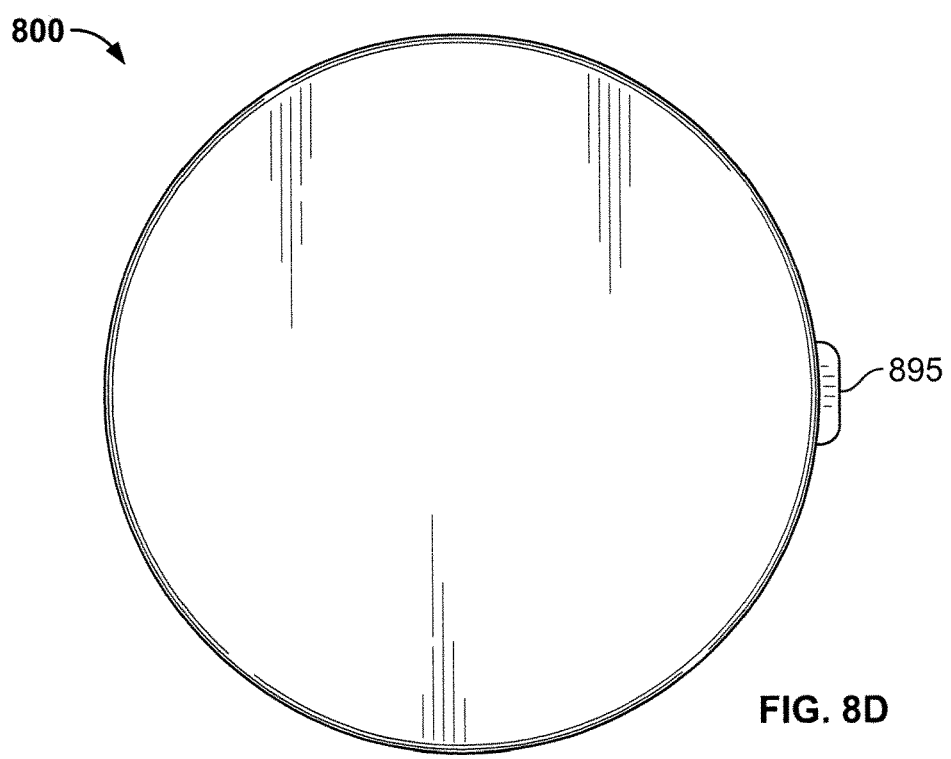
Figure 8E:
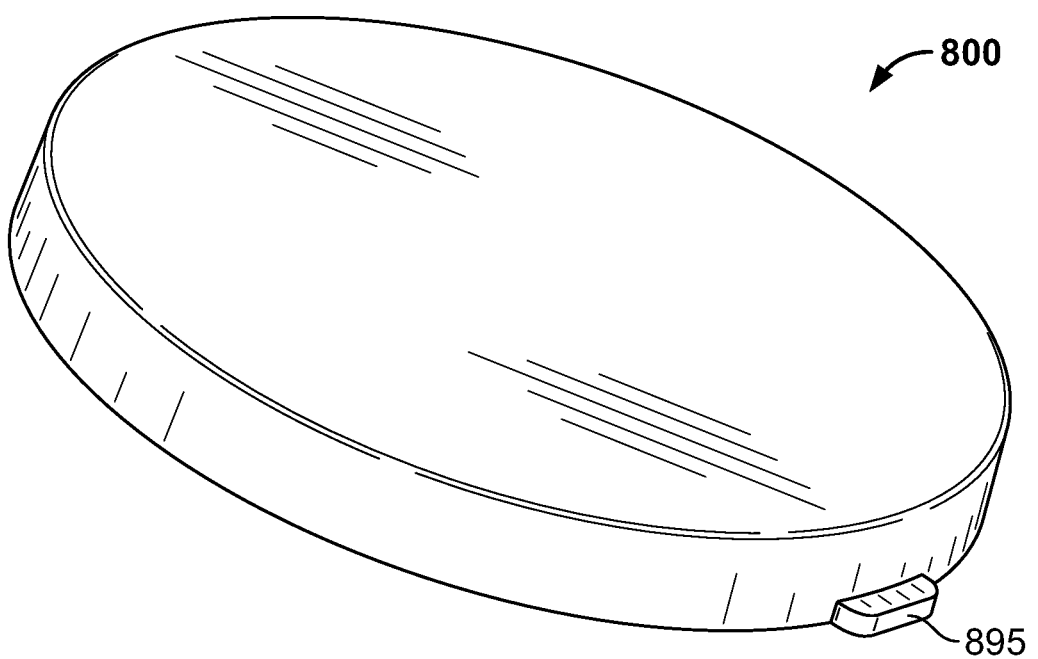
FIG. 8E is a schematic bottom perspective view of the exemplary adaptor of FIG. 8A.

In FIGS. 7A and 7C, base 510 is shown without a fluid permeable membrane support. In FIG. 5E, the permeable member 585 is shown in the cell capture system disposed underneath membrane 540.

In certain embodiments, the cell capture system, in particular the porous membrane 240, has a sterility assurance level less than $10^{-6}$, $10^{-7}$, $10^{-8}$, or $10^{-9}$. This can be achieved, for example, by sterilizing the cell capture system 100 or 500, via techniques known in the art, for example, via autoclaving, exposure to ionizing radiation, for example, gamma radiation or exposure to a sterilizing fluid or gas, for example, ethylene oxide or vaporized hydrogen peroxide. The cell capture system 100 can be enclosed within a receptacle (e.g., a bag), prior to, during, or after sterilization. The cell capture system 100 can be placed within a receptacle (e.g., a bag) and sealed (e.g., hermetically sealed) before terminal sterilization (e.g., via exposure to ionizing radiation).

(II) Cell Capture System Manufacture and Assembly

The cell capture systems 100 and 500, and their various components, can be made and assembled using known techniques, including injection molding and machining. While the techniques are described below with respect to the cell capture system 100, the same techniques can be used for the cell capture system 500 and its components. The cup 105 and the base 110 may be made out of any substantially rigid material capable of being sterilized. For example, the cup can be fabricated from materials known in the art, for example, plastics and metals, which may vary depending upon a number of factors, for example, ease of manufacture, cost, and the coupling system employed. For example, when the upper portion 230 and the ring 235 are integral components of the cup separated by a frangible connection, the upper portion and ring can be molded, for example, injection molded, using a polymer material, e.g., polyethylene or polypropylene.

In one approach, the cup 110 with the upper portion 230 and the ring 235 can be manufactured as one or more parts. Then membrane 240 is secured to the ring 235 about a periphery thereof, prior to positioning the cup 105 within the base 110. It is understood, however, that depending upon the embodiment and securing mechanism, the membrane may be attached to the periphery of the ring prior to the ring 235 being attached to the upper portion 230 of the cup. Thereafter, the resulting ring and membrane assembly can then be attached to the upper portion of the cup via a connection such as a threadable connection, a bayonet connection or an interference fit connection.

The various components can be a wide variety of sizes while still being within the scope of the invention. In certain embodiments, the cell capture system 100 is between about 1 inch and 5 inches tall (e.g., approximately 3 inches), with a diameter of between about 1 inch and 3 inches (e.g., approximately 2.25 inches). The cell capture system 100 may be sized to hold from about 100 mL to about 200 mL of the fluid sample, although different sizes may be used to hold more or less fluid.

As described above, a registration feature between the ring 235 and the base 110 may be used, so the step of positioning the cup 105 in the base 110 puts the cup 105 in a predetermined circumferential orientation relative to the base 110. If the support 285 is included, it should be placed in the recess 280 prior to positioning the cup 105 in the base 110.

(III) Cell Capture Method

As described above, FIGS. 1A-1F depict the components of an exemplary cell capture system 100, and FIGS. 5A-5F depict similar components of an exemplary cell capture system 500. The description below with respect to the method of using the cell capture system 100 is also applicable to the cell capture system 500. The cup 105 is coupled to the base 110 through the interface between the ring 235 and the base 110. The lid 115 may be provided on top of the cup 105 to protect the interior of the cup 105 from being contaminated.

During use, in order to capture/harvest cells, a fluid sample is applied (e.g., poured) into the cup 105. Due to the tapers of the upper portion 105, the fluid wets and passes through the membrane 240. The fluid typically passes through the membrane assembly (e.g., through the membrane 240, and the support 285, if one is used) toward the base 110. Negative pressure, for example, a vacuum, can be used to draw fluid through the membrane 240 to the openings 290, and to help keep the membrane 240 substantially flat. The fluid application step can occur before, at the same time, or after application of the vacuum. It is contemplated that the substantially non-autofluorescent membrane 240 permits a flow rate therethrough of at least 5 or at least 10 mL/cm$^2$/min with a vacuum of about 5 Torr or about 10 Torr.

After the fluid is drawn through the cell capture system 100, any particles and/or cells in the fluid that cannot pass through the membrane 240 are retained on the upper exposed surface of the membrane 240. After pouring the fluid into the cup assembly 100, the upper portion 230 may be separated from the ring 235, with the resulting assembly depicted in FIGS. 4A-4F (with an optional lid 405 and a plug 410).

To separate the upper portion 230 from the ring 235, the user may apply a sufficient force to break the connection. When the upper portion 230 and the ring 235 are integrally formed, as in the exemplary embodiment, the user may twist the cup 105 relative to the base 110. Based on the overlap between the protrusions 260 and the notches 270 providing resistance to such rotation, the upper portion 230 will separate from the ring 235 along parting plane 250. The force required depends on a number of factors, including the thickness of the frangible connection 245, and the cell capture system 100 is typically designed to require at least 5-20 inch pounds (0.56-2.26 newton meters). The lid 405 may be placed on top of the base 110 to protect the moistened membrane 240 and support 285 from contamination when the base 110 is transferred to a detection system, or when the base 110 containing the membrane 240 is incubated, for example, for 15 minutes to 8 hours to permit the captured viable cells to proliferate. The plug 410 can be secured to a bottom of the base 110, for example, via finger protrusion 295, to prevent any leakage of residual fluid, particularly when the base 110 is inserted into other equipment, for example, into a stage that is itself introduced into the detection system.

In another embodiment, the rings 235, 535 can be placed onto an adapter 800 (see FIGS. 8A-8E) following removal from the respective cell capture system 100 or 500. The adapter 800 can have similar notches 270 as the bases 110, 510, allowing for the rings 235, 535 to be held securely. Many different patterns for the notches 270 can be used, including those depicted in the bases 110, 510, though any complementary pattern to the protrusions 260, 660 on the rings 235, 535 may be used. As described above, a unique notch 270' may be used to uniquely orient the rings 235, 535 when disposed on the adapter 800. A registration feature 895 (e.g., a protrusion) can be located the adaptor 800 to orient the adaptor 800 when placed in the scanning system (e.g., mated with a stage with a matching pattern to ensure proper orientation). As the rings 235, 535 can be uniquely oriented within the adapter 800, and the adapter 800 can be uniquely oriented within the scanning system, the membranes 240, 540 can have a consistent and known orientation during scanning. Further, a raised portion 885 may function similarly as the support members 285, 585, namely by providing a surface on which a lower surface (i.e., the side without the cells) of the membranes 240, 540 may interface to maintain planarity of an upper surface (i.e., the side with the cells) of the membranes 240, 540 during scanning.

Figure 9A:
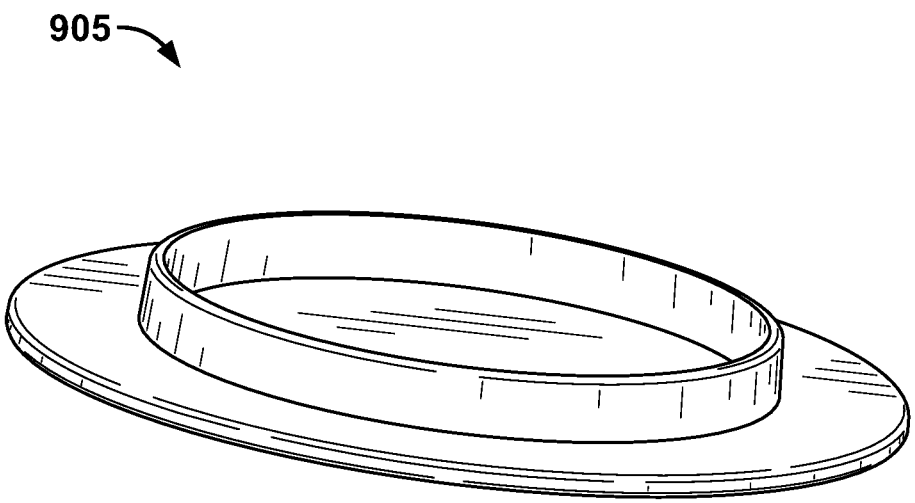
FIG. 9A is a schematic bottom perspective view of an exemplary lens for use with the exemplary adapter of FIG. 8A.
Figure 9B:
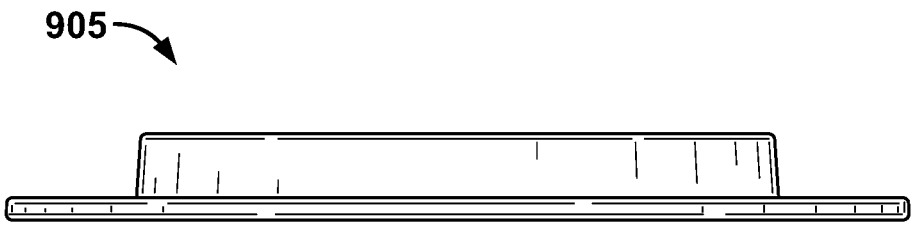
FIGS. 9B-9D are schematic side, bottom, and top views, respectively, of the exemplary lens of FIG. 9A.
Figure 9C:
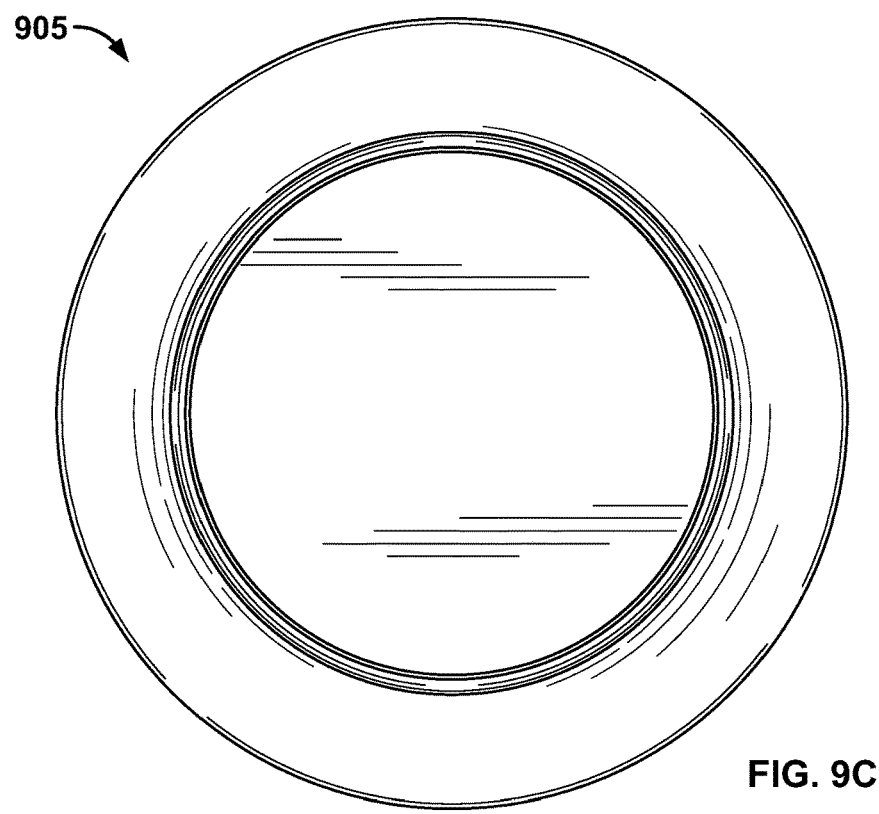
Figure 9D:
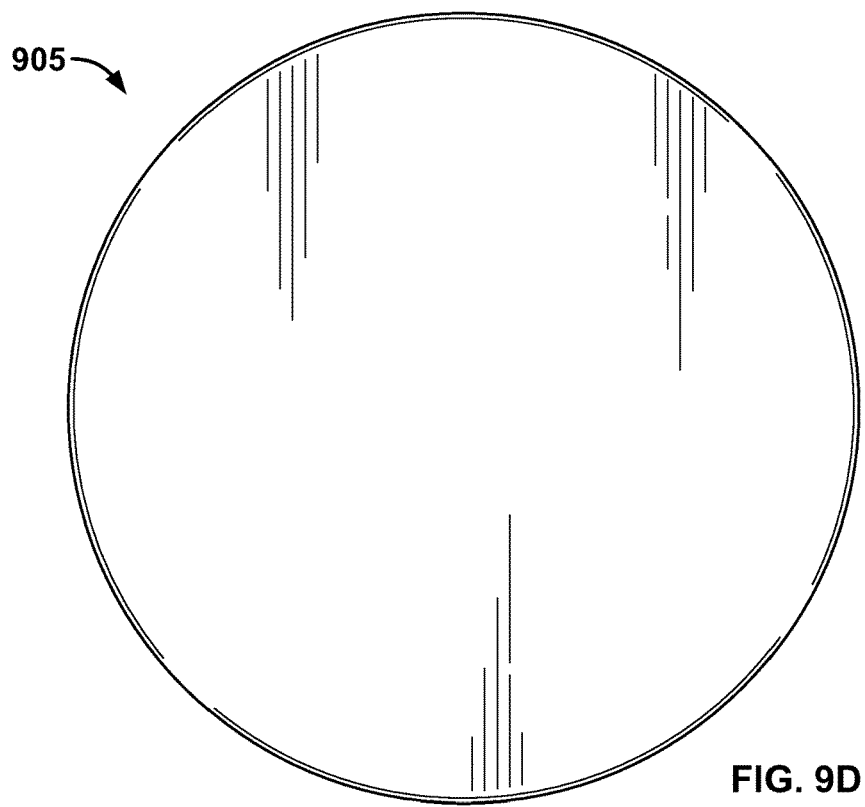
Figure 9E:
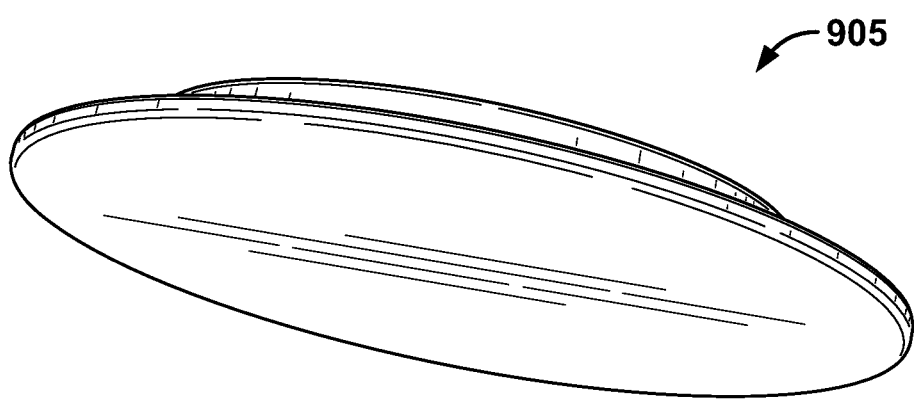
FIG. 9E is a schematic top perspective view of the exemplary lens of FIG. 9A.

Similar to the lid 405 (depicted in phantom in FIG. 4A), a lens 905 (depicted in FIGS. 9A-9E) may be used with the adaptor 800 to cover the contents therein (e.g., the membranes 240, 540) to prevent contamination. In some embodiments, the lens 905 may be removed during scanning, while in other embodiments the lens 905 may remain on the adaptor 800 during scanning. A lower surface of the lens 905 may have one or more features for mating with the adaptor 800, such as the depicted wall in FIGS. 9A-9C. The wall can rest in a space between an inside wall and an outside wall of the adaptor 800, helping ensure stability of the lens 900 and full coverage of the membranes 240, 540 during scanning. An upper surface of the lens 900 may be substantially flat or arcuate, and can be controlled to ensure proper scanning results.

The cells can be stained at any point after capture with a viability stain or a viability staining system, for example, as discussed in U.S. patent application Ser. No. 13/875,969, so that it is possible to selectively detect and distinguish viable cells from non-viable cells. The cells may optionally be washed with a physiologically acceptable salt and/or buffer solution to remove residual non-specifically bound fluorescent dye and/or quencher.

Once the cell capture system has been used to capture cells originally present in the fluid sample, and the cells stained as appropriate, the resulting membrane (still attached to the ring) can be inserted into a stage (see, U.S. patent application Ser. No. 13/875,969) for insertion into a suitable detection system. Exemplary detection systems are described, for example, in International Patent Application No. PCT/IB2010/054965, filed Nov. 3, 2010, U.S. patent application Ser. No. 13/034,402, filed Feb. 24, 2011, International Patent Application No. PCT/IB2010/054966, filed Nov. 3, 2010, U.S. patent application Ser. No. 13/034,380, filed Feb. 24, 2011, International Patent Application No. PCT/IB2010/054967, filed Nov. 3, 2010, and U.S. patent application Ser. No. 13/034,515, filed Feb. 24, 2011. Other patent applications directed to such systems include U.S. Patent Publication Nos. US2013/0316394, US2013/0309686, US2013/0323745, and US2013/0316363.

INCORPORATION BY REFERENCE

The entire disclosure of each of the patent documents and scientific articles referred to herein or attached hereto in the appendix is incorporated by reference for all purposes. The entire description of U.S. Provisional Patent Application Ser. Nos. 61/641,805; 61/641,809; 61/641,812; 61/784,759; 61/784,789; and 61/784,807 and U.S. patent application Ser. Nos. 13/875,914; 13/875,936; 13/875,969 and 13/886,004 are incorporated by reference herein for all purposes.

EQUIVALENTS

The invention may be embodied in other specific forms without departing from the spirit or essential characteristics thereof. The foregoing embodiments are therefore to be considered in all respects illustrative rather than limiting the invention described herein. Various structural elements of the different embodiments and various disclosed method steps may be utilized in various combinations and permutations, and all such variants are to be considered forms of the invention. Scope of the invention is thus indicated by the appended claims rather than by the foregoing description, and all changes that come within the meaning and range of equivalency of the claims are intended to be embraced therein.

What is claimed is:

1. A cell capture system for receiving a fluid sample, the system comprising:
   (a) a cup comprising:
      (i) an upper portion,
      (ii) a ring having a periphery, wherein the upper portion is separably coupled to the ring by a frangible connection comprising a circumferential groove that defines a parting plane between the upper portion and the ring so that the upper portion can be separated from the ring upon manual application by a user of a rotational force sufficient to break the frangible connection, and
      (iii) a fluid permeable membrane attached to the periphery to produce a fluidic seal between the membrane and the ring, wherein a portion of the membrane is adapted to retain cells thereon; and
   (b) a base configured to receive the ring.

2. The system of claim 1, wherein the membrane portion (i) defines a plurality of pores having an average diameter less than about 1 µm so as to permit fluid to traverse the portion of the membrane while retaining cells thereon and (ii) is substantially non-autofluorescent when exposed to light having a wavelength in a range from about 350 nm to about 1000 nm.

3. The system of claim 1, wherein the membrane portion has a flatness tolerance of up to about 100 µm.

4. The system of claim 1, wherein the cup is adapted to direct a fluid, when introduced into the upper portion, toward the membrane portion.

5. The system of claim 1, wherein the ring is integrally formed with the upper portion.

6. The system of claim 1, wherein the frangible connection comprises a thin wall at an intersection of the upper portion and the ring.

7. The system of claim 1, wherein the ring comprises a circumferential registration feature.

8. The system of claim 1, wherein the membrane is at least one of adhered, bonded, heat welded, and ultrasonically welded to the ring.

9. The system of claim 1, wherein the base defines a recess adapted to receive a membrane support.

10. The system of claim 9, wherein the recess defines a plurality of openings adapted to permit the passage of fluid therethrough.

11. The system of claim 1, wherein the base comprises a registration feature.

12. The system of claim 11, wherein the registration feature comprises a depression defined by a surface of the base.

13. The system of claim 1, wherein the cup further comprises at least one latch adapted to couple the cup to the base.

14. The system of claim 13, wherein the at least one latch is adapted to resist separation of the cup and the base in a plane perpendicular to a parting plane.

15. A method of harvesting cells if present in a fluid sample, the method comprising:
   (a) introducing the fluid sample to the upper portion of the cup of claim 1; and
   (b) permitting the fluid to pass through the membrane portion.

16. The method of claim 15, further comprising, after applying the fluid, separating the upper portion from the ring.

17. The method of claim 16, wherein separating the upper portion from the ring comprises applying a force sufficient to decouple the ring from the upper portion.

18. The method of claim 17, wherein applying the force comprises twisting the cup relative to the base.

19. A method of manufacturing a cell capture system of claim 1, the method comprising the steps of:
   (a) providing a ring having a periphery;
   (b) securing a fluid permeable member to a periphery to produce a fluidic seal between the membrane and the ring; and
   (c) positioning the ring having the membrane secured thereto within a base configured to receive the ring.

20. The method of claim 19, wherein, prior to step (b), the ring is separably coupled to the upper portion.

21. The method of claim 19, wherein the positioning step comprises mating the cup with the base in a predetermined circumferential orientation.

22. The method of claim 19, further comprising, prior to positioning the cup within the base, placing a porous support in a recess formed in the base.

* * * * *